US010591751B2

(12) United States Patent
Hyde et al.

(10) Patent No.: US 10,591,751 B2
(45) Date of Patent: *Mar. 17, 2020

(54) OPHTHALMIC DEVICES AND RELATED METHODS

(71) Applicant: Elwha LLC, Bellevue, WA (US)

(72) Inventors: Roderick A. Hyde, Redmond, WA (US); John Marshall, Farnborough (GB); Clarence T. Tegreene, Mercer Island, WA (US); Roger Zaldivar, Mendoza (AR); Roberto Zaldivar, Mendoza (AR)

(73) Assignee: ELWHA LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/113,545

(22) Filed: Aug. 27, 2018

(65) Prior Publication Data

US 2018/0364500 A1     Dec. 20, 2018

Related U.S. Application Data

(63) Continuation of application No. 15/221,366, filed on Jul. 27, 2016, now Pat. No. 10,078,231.

(51) Int. Cl.
    *G02C 7/02*          (2006.01)
    *G02C 7/04*          (2006.01)
    (Continued)

(52) U.S. Cl.
    CPC ................ *G02C 7/083* (2013.01); *A61F 2/16* (2013.01); *G02C 7/022* (2013.01); *G02C 7/04* (2013.01);
    (Continued)

(58) Field of Classification Search
    CPC . G02C 7/02; G02C 7/083; A61F 2/613; A61F 2/1624
    (Continued)

(56) References Cited

U.S. PATENT DOCUMENTS 6,638,304 B2    10/2003    Azar
7,041,133 B1    5/2006    Azar
(Continued)

OTHER PUBLICATIONS

U.S. Appl. No. 14/807,673, filed Jul. 23, 2015.
(Continued)

*Primary Examiner* — Darryl J Collins
(74) *Attorney, Agent, or Firm* — Dorsey & Whitney LLP

(57) ABSTRACT

Embodiments disclosed herein relate to systems including at least one ophthalmic device and methods of using the system. The ophthalmic device includes at least one switchable lens therein that includes at least one electro-optical material. The ophthalmic device also includes at least one charging electrical circuitry. The charging electrical circuitry is electrically coupled to the switchable lens and is configured to receive electrical energy from or provide electrical energy to the switchable lens. The ophthalmic device can also include at least one transfer electrical circuitry that can be coupled to and configured to transfer electrical energy between the charging electrical circuitry and the switchable lens. The ophthalmic device can also include at least one controller operably coupled to at least the charging electrical circuitry and the transfer electrical circuitry. The controller can be configured to at least partially control the charging electrical circuitry and the transfer electrical circuitry.

32 Claims, 11 Drawing Sheets

(51) Int. Cl.
  *A61F 2/16* (2006.01)
  *G02C 7/08* (2006.01)
  *G02C 7/10* (2006.01)
  *G02C 7/12* (2006.01)

(52) U.S. Cl.
  CPC .............. *G02C 7/101* (2013.01); *G02C 7/12* (2013.01); *A61F 2/1624* (2013.01); *A61F 2002/1681* (2013.01); *G02C 2202/16* (2013.01); *G02C 2202/20* (2013.01)

(58) Field of Classification Search
  USPC .............. 351/159.03, 159.39; 623/6.11, 6.22
  See application file for complete search history.

(56) References Cited

U.S. PATENT DOCUMENTS

| | | | |
|---|---|---|---|
| 8,043,370 | B2 | 10/2011 | Bretthauer et al. |
| 8,216,309 | B2 | 7/2012 | Azar |
| 8,992,610 | B2 | 3/2015 | Blum et al. |
| 9,254,189 | B2 | 2/2016 | Azar |
| 9,268,155 | B2 | 2/2016 | Pugh et al. |
| 10,078,231 | B2 * | 9/2018 | Hyde .................. A61F 2/16 |
| 2003/0018383 | A1 | 1/2003 | Azar |
| 2006/0206205 | A1 | 9/2006 | Azar |
| 2007/0260307 | A1 | 11/2007 | Azar |
| 2009/0105817 | A1 | 4/2009 | Bretthauer et al. |
| 2009/0251660 | A1 | 10/2009 | Figler et al. |
| 2009/0326652 | A1 | 12/2009 | Azar |
| 2010/0324408 | A1 | 12/2010 | Klink et al. |
| 2012/0162600 | A1 | 6/2012 | Pugh et al. |
| 2012/0239144 | A1 | 9/2012 | Azar |
| 2013/0073038 | A1 | 3/2013 | Azar |
| 2014/0002789 | A1 | 1/2014 | Pugh et al. |
| 2015/0057748 | A1 | 2/2015 | Azar |
| 2015/0138454 | A1 | 5/2015 | Pugh et al. |
| 2018/0031865 | A1 | 2/2018 | Hyde et al. |

OTHER PUBLICATIONS

U.S. Appl. No. 14/807,719, filed Jul. 23, 2015.
U.S. Appl. No. 14/807,756, filed Jul. 23, 2015.
U.S. Appl. No. 15/221,366, filed Jul. 27, 2016.
Argal, "Newer intraocular lens materials and design", Journal of Clinical Ophthalmology and Research, vol. 1—Issue 2, May-Aug. 2013, pp. 113-117.
Findl, "Intraocular Lens Materials and Design", Achieving Excellence in Cataract Surgery, Chapter 12, 2009, pp. 95-108.
Palumbo, et al., "Charge Pump Circuits: An Overview on Design Strategies and Topologies", IEEE Circuits and Systems Magazine, First Quarter, 2010, pp. 31-45.
Plyarinos, et al., "Charge Pumps: An Overview", Department of Electrical and Computer Engineering, University of Toronto, 2003, pp. 1-7.
Tetz, et al., "New Hydrophobic IOL Materials and Understanding the Science of Glistenings", Current Eye Research, ISSN: 0271-3683 print/1460-2202 online, Published online, Jan. 26, 2015, pp. 969-981.
Tripti, et al., "Materials for intraocular lenses (IOLs): Review of developments to achieve biocompatibility", e-Polymers 2009, No. 124, ISSN 1618-7229, Oct. 27, 2009, pp. 1-23.
Chinese State Intellectual Property Office, Notification of the Second Office Action, App. No. 201680055694.6 (based on PCT App. No. PCT/US2016/043065); dated Oct. 8, 2019; pp. 1-4 (machine translation provided).

* cited by examiner

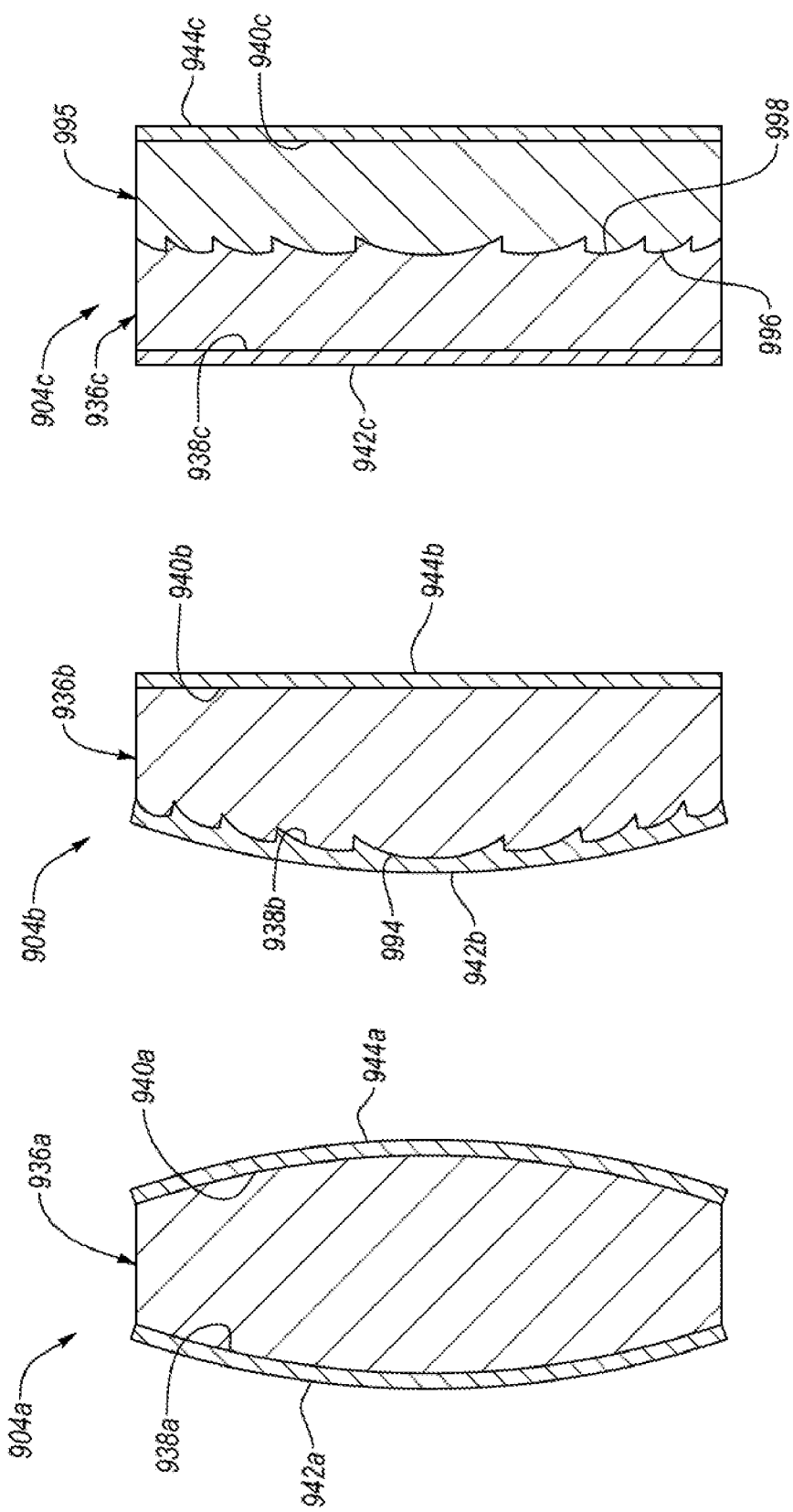

OPHTHALMIC DEVICES AND RELATED METHODS

PRIORITY APPLICATIONS

For purposes of the USPTO extra-statutory requirements, the present application constitutes a continuation of U.S. patent application Ser. No. 15/221,366, entitled OPHTHALMIC DEVICES AND RELATED METHODS, naming Roderick A. Hyde, John Marshall, Clarence T. Tegreene, Roger Zaldivar, and Roberto Zaldivar as inventors, filed 27, Jul. 2016, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

BACKGROUND

Focal correction can improve vision of an individual. For example, glasses, contact lenses, and intraocular lenses (IOLs), such as pseudophakic IOLs, aphikic IOLs, or phakic IOLs (PIOLS), can be used to correct the vision of an individual.

Typical IOLs can include monofocal, multifocal, or accommodative configurations. IOLs can include an optic element (e.g., lens) and haptic elements (e.g., arms or wings configured to aid in positioning the IOL). Such configurations can be limited to focusing either on near or far vision without selectively modifiable adjustment therebetween.

SUMMARY

Embodiments disclosed herein relate to systems including at least one ophthalmic device and methods of using the system. The at least one ophthalmic device includes at least one switchable lens having at least one electro-optical material. The at least one electro-optical material is configured to change at least one optical property thereof responsive to an electric field. The at least one ophthalmic device also includes at least one charging electrical circuitry. The at least one charging electrical circuitry is electrically coupled to the at least one switchable lens and is configured to receive electrical energy from or provide electrical energy to the at least one switchable lens. As such, the electrical energy used to apply an electric field to the at least one electro-optical material does not need to be discharged or otherwise dissipated from the at least one ophthalmic device when the electric field applied to the at least one electro-optical material is decreased. The at least one ophthalmic device can also include at least one transfer electrical circuitry. The at least one transfer electrical circuitry is coupled to the charging electrical circuitry and the at least one switchable lens. The at least one transfer electrical circuitry can be configured to selectively and controllably transfer electrical energy between the at least one charging electrical circuitry and the at least one switchable lens. The at least one ophthalmic device can also include at least one controller operably coupled to at least the charging electrical circuitry and the transfer electrical circuitry. The at least one controller can be configured to at least partially control the at least one charging electrical circuitry and the at least one transfer electrical circuitry, such as controlling an amount of electrical energy transferred between the at least one charging electrical circuitry and the at least one switchable lens.

In an embodiment, a system is disclosed. The system includes at least one ophthalmic device. The at least one ophthalmic device includes at least one switchable lens including at least one electro-optical material disposed between a first electrode and a second electrode. The at least one ophthalmic device also includes at least one charging electrical circuitry coupled to the first electrode and the second electrode. The at least one charging electrical circuitry is configured to store electrical energy from the first electrode and the second electrode. Additionally, the at least one ophthalmic device includes at least one transfer electrical circuitry coupled to the at least one charging electrical circuitry, the first electrode, and the second electrode. The system also includes at least one controller operably coupled to the at least one transfer electrical circuitry and the at least one charging electrical circuitry.

In an embodiment, a method of modifying at least one optical property of at least one switchable lens is disclosed. The method includes transferring at least some electrical energy stored between a first electrode and a second electrode of the at least one switchable lens to at least one charging electrical circuitry. The at least one switchable lens can include an electro-optical material disposed between the first electrode and the second electrode.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 9A-9C are schematic cross-sectional side views of different switchable lenses that can be used in any of the ophthalmic devices disclosed herein, according to various embodiments.

DETAILED DESCRIPTION

Embodiments disclosed herein relate to systems including at least one ophthalmic device and methods of using the system. The at least one ophthalmic device includes at least one switchable lens therein that includes at least one electro-optical material. The at least one electro-optical material is configured to change at least one optical property thereof responsive to an electric field. The at least one ophthalmic device also includes at least one charging electrical circuitry ("CEC"). The CEC is electrically coupled to the at least one switchable lens and is configured to receive electrical energy from or provide electrical energy to the at least one switchable lens. As such, the electrical energy used to apply an electric field to the at least one electro-optical material does not need to be discharged or otherwise dissipated from the at least one ophthalmic device when the electric field applied to the at least one electro-optical material is decreased. The ophthalmic device can also include at least one transfer electrical circuitry ("TEC"). The TEC is coupled to the CEC and the at least one switchable lens. The TEC can be configured to selectively and controllably transfer electrical energy between the CEC and the at least one switchable lens. The at least one ophthalmic device can also include at least one controller operably coupled to at least the CEC and the TEC. The at least one controller can be configured to at least partially control the CEC and the TEC, for example, to control the amount of electrical energy transferred between the CEC and the switchable lens.

Figure 1:
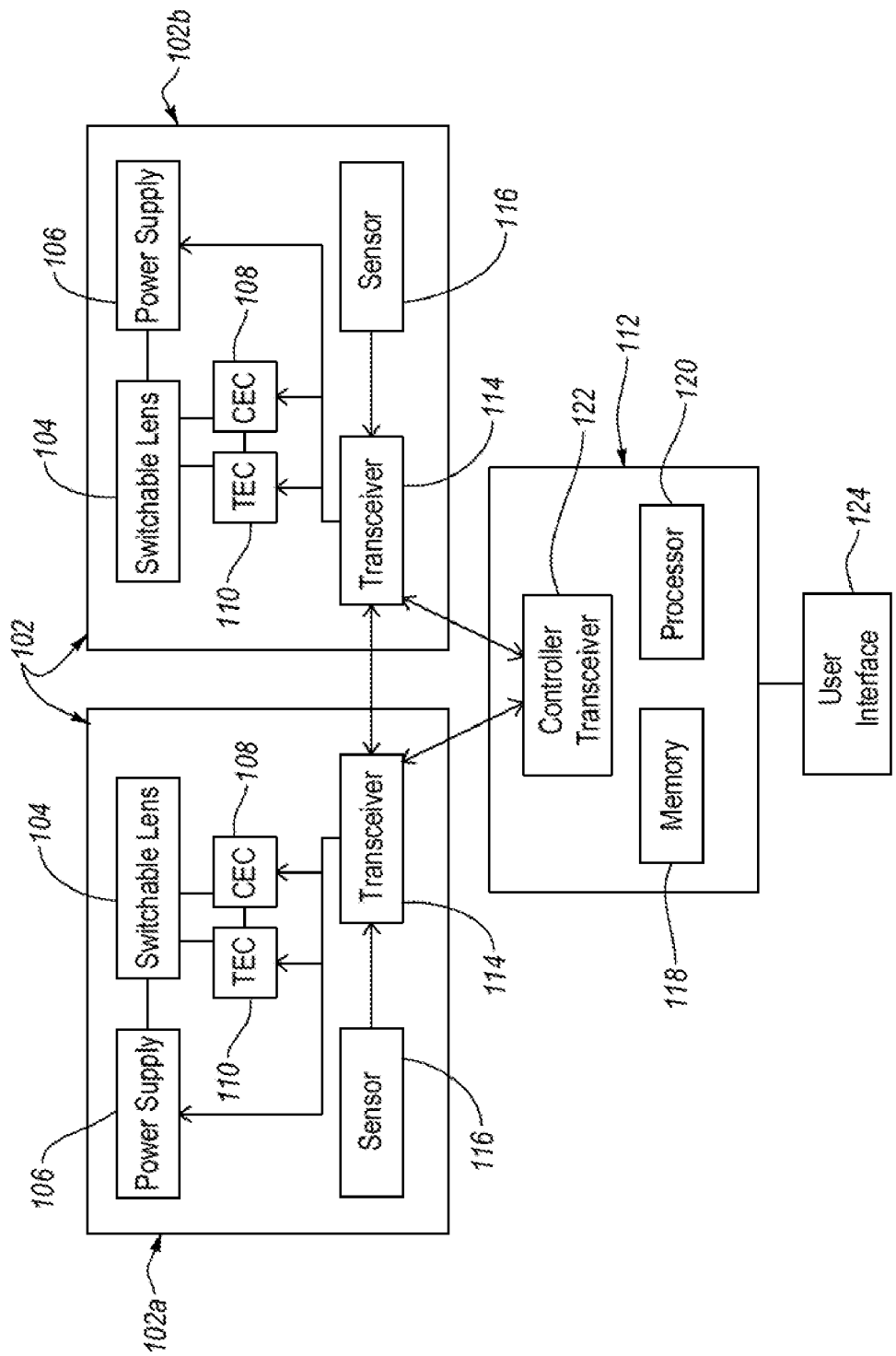
FIG. 1 is a functional block diagram of a system including at least one ophthalmic device, according to an embodiment.

FIG. 1 is a functional block diagram of a system 100 including at least one ophthalmic device 102 (e.g., a first or second ophthalmic device 102a, 102b), according to an embodiment. The ophthalmic device 102 includes at least one switchable lens 104. The switchable lens 104 is configured to selectively modify at least one optical property thereof (e.g., a focal length) when the switchable lens is at least partially charged (e.g., an electrical field is applied to the switchable lens 104 or the electrical field is increased) or at least partially discharged (e.g., an electric field is removed from the switchable lens or the electrical field is decreased). For example, the ophthalmic device 102 includes at least one power source 106 electrically coupled to the switchable lens 104. The power source 106 is configured to provide electrical energy to the switchable lens 104 that is used to at least partially charge the switchable lens 104. In the illustrated embodiment, each of the ophthalmic devices 102 is shown with its own power source 106. However, in other embodiments, a common power source can be provided to provide power to each ophthalmic devices 102.

The ophthalmic device 102 includes at least one CEC 108 electrically coupled to the switchable lens 104. The CEC 108 is configured to receive electrical energy from the switchable lens 104 when the switchable lens is at least partially discharged. The electrical energy received by the CEC 108 can provide electrical power to one or more components of the ophthalmic device 102. In other words, the CEC 108 enables the system 100 to reuse the electrical energy stored in the switchable lens 104 after the switchable lens 104 is at least partially discharged. The system 100 further includes at least one TEC 110 coupled to and electrically positioned between the switchable lens 104 and the CEC 108. The TEC 110 is configured to enable transfer of the electrical energy between the switchable lens 104 and the CEC 108. In an embodiment, one or more components of the system 100 (e.g., the switchable lens 104, the power source 106, the CEC 108, or the TEC 110) can operate responsive to direction from at least one controller 112.

Figure 10A:
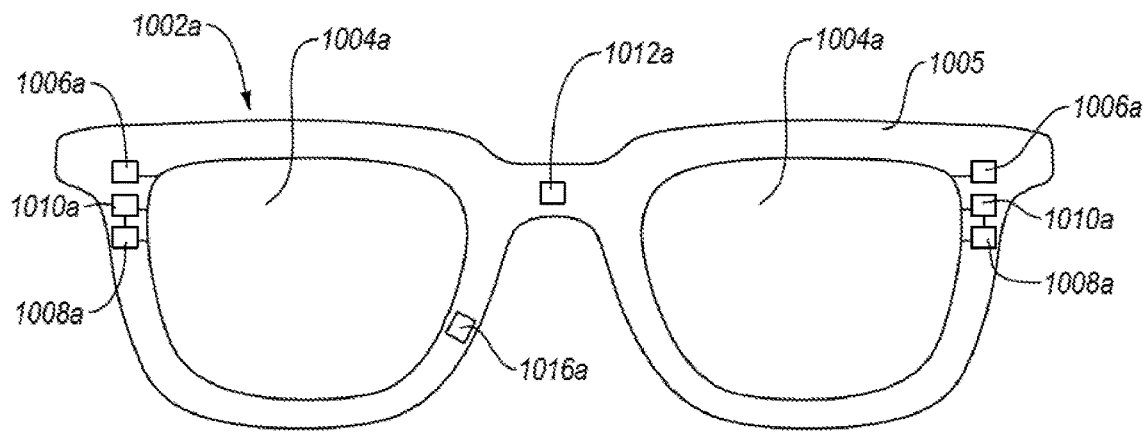
FIGS. 10A-10C are schematic illustrations of different ophthalmic devices, according to various embodiments.
Figures 10B, 10C:
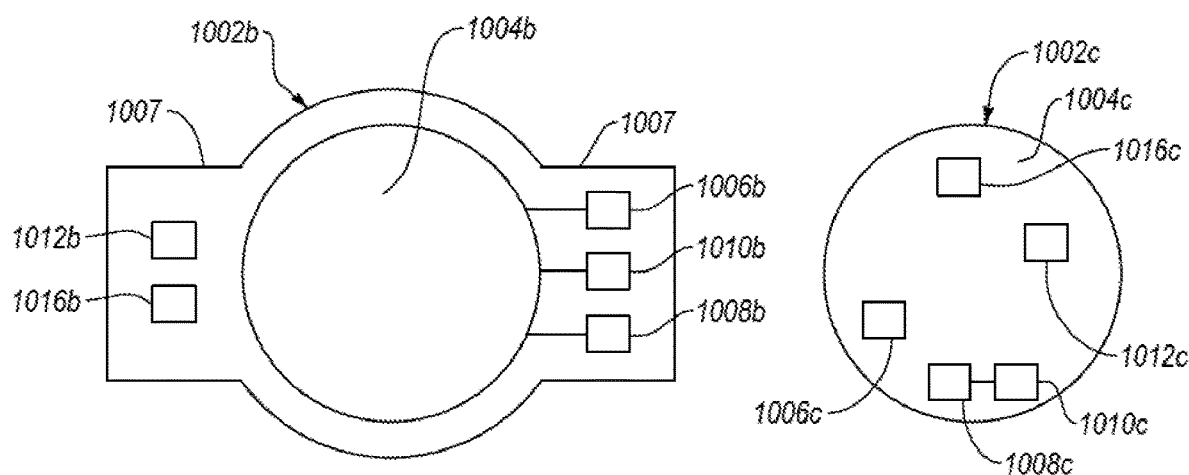

The ophthalmic device 102 can include any device configured to correct, improve, or otherwise effect an individual's vision. For example, the ophthalmic device 102 can include at least one spectacle (FIG. 10A), at least one intraocular lens (FIG. 10B), or at least one contact lens (FIG. 10C).

In an embodiment, the system 100 can include a single ophthalmic device 102. In an embodiment, the system 100 can include a plurality of ophthalmic devices. For example, the system 100 can include the first ophthalmic device 102a and the second ophthalmic device 102b. The first ophthalmic device 102a can be configured to be positioned above, on, or in a first eye of the individual and the second ophthalmic device 102a can be configured to provide a visual effect to a second eye of the individual. For example, the first and second ophthalmic devices 102a, 102b can be configured to be positioned above, on, or in the first and second eyes, respectively.

In an embodiment, the first and second ophthalmic devices 102a, 102b can be configured substantially the same. For example, each of the first and second ophthalmic devices 102a, 102b can include a switchable lens 104, a power source 106, a CEC 108, and a TEC 110. In an embodiment, the first and second ophthalmic devices 102a, 102b can be different. For example, the first ophthalmic device 102a can include a switchable lens 104 and the second ophthalmic device 102b can include a non-switchable lens. In another example, the first ophthalmic device 102a can include at least one component that is omitted from the second ophthalmic device 102b or vice versa. In another example, the first and second ophthalmic devices 102a, 102b can function differently.

In an embodiment, the first and second ophthalmic devices 102a, 102b can be communicably coupled together. For example, the first and second ophthalmic devices 102a, 102b can include at least one transceiver 114 that communicably couples the first and second ophthalmic devices 102a, 102b together. The transceivers 114 can also communicably coupled the first and second ophthalmic devices 102a, 102b to other components of the system 100 (e.g., the controller 112 when the controller 112 is remote from the first or second ophthalmic devices 102a, 102b). Communicably coupling the first and second ophthalmic devices 102a, 102b together allows the first and second ophthalmic devices 102a, 102b to transmit information therebetween or to other devices spaced therefrom (e.g., the controller 112). The information can include status updates, one or more characteristics sensed by one or more sensors 116 of the first or second ophthalmic devices 102a, 102b, or any other suitable information.

The ophthalmic device 102 and, more particularly, the switchable lens 104 can be configured to exhibit a switchable or modifiable optical property responsive to an electric field being applied thereto. In an embodiment, the switchable lens 104 can include at least one electro-optical material. The electro-optical material can include at least one of a liquid crystal, an electro-optic polymer, an electro-optic crystal, an electro-chromic material, or another suitable material. For example, the electro-optical material can include lithium niobate, lithium tantalite, a liquid crystal, or another electro-optical material. For example, the electro-optical material can include a material that selectively or controllably changes a refractive index, changes a transmissivity, changes a spectral filter property (e.g., changes from a high pass filter to a low pass filter), or causes a phase shift responsive to an electrical field. In another example, the electro-optical material of the switchable lens 104 can selectively or controllably change a focal length thereof responsive to an electrical field. In an embodiment, the switchable lens 104 can include a plurality of electro-optical materials, such as at least a first electro-optical material and a second electro-optical material. The first electro-optical material can be different from or similar to the second electro-optical material. In an embodiment, the switchable lens 104 can include a passive material (e.g., a substantially electro-optically inert material) having a substantially fixed index of refraction (e.g., glass, polymethylmethacrylate, silicone (e.g., hydrophobic silicone such as polydimethoxysilicone), hydrophobic acrylic (e.g., foldable hydrophobic acrylic), hydrophilic acrylic, electro-optical inert hydrophilic materials, etc.).

Figure 2:
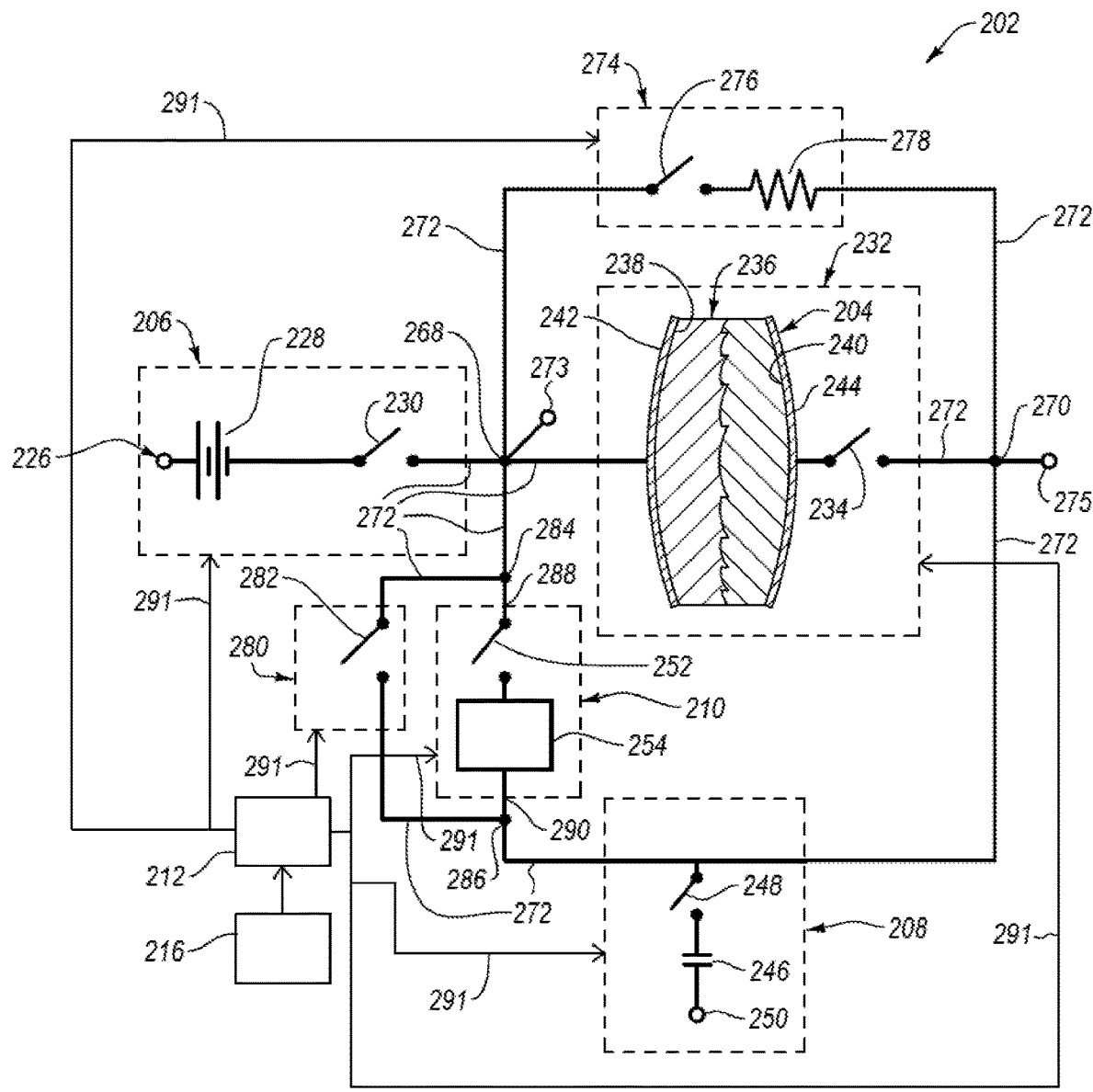
FIG. 2 is an electrical diagram illustrating at least some of the components of an ophthalmic device, according to an embodiment.

The switchable lens 104 can include a first electrode (e.g., first electrode 242 of FIG. 2) and a second electrode (e.g., second electrode 244 of FIG. 2). The first and second electrodes can be positioned such that the at least one electro-optical material is disposed between the first and second electrodes. The first and second electrodes can be configured to apply an electric field to the electro-optical material and store electrical energy therebetween. In an embodiment, the first and second electrodes can be formed of an electrically conductive material that is at least partially transparent to visible wavelength light.

In an embodiment, the switchable lens 104 can be configured to selectively switch or modify a focal length thereof. For example, the switchable lens 104 can be switchable between a first focal length and a second focal length. The switchable lens 104 can exhibit the first focal length when a first electrical field is applied to the electro-optical material and a second focal length when a second electrical field is applied to the electro-optical material, where the second electrical field is greater than the first electrical field. For example, the first electrical field can be zero (e.g., the switchable lens 104 exhibits the first focal length when in its inactivated, ground state and exhibits the second focal length in its activated state). In another example, the first electrical field can be greater than zero (e.g., the switchable lens 104 exhibits the first focal length when in its first activated state and exhibits the second focal length in its second activated state). In an embodiment, the switchable lens 104 can exhibit one or more additional focal lengths when at least one additional electrical field is applied to the electro-optical material of the switchable lens 104. The one or more additional focal lengths can have a magnitude between the first and second focal lengths. The additional electric field can be between the first and second electrical fields.

The at least one CEC 108 can be electrically coupled to the switchable lens 104 (e.g., electrically coupled to the first and second electrodes of the switchable lens 104). The CEC 108 can include suitable electrical circuitry that is configured to controllably receive electrical energy from the first and second electrodes, controllably transmit the electrical energy to another component of the system 100, or store the electrical energy from the first and second electrodes. The CEC 108 includes at least one energy storage device that is configured to store electrical energy therein. The energy storage device can include a battery (e.g., microbattery), at least one capacitor, or another suitable energy storage device. In an embodiment, the CEC 108 can include a plurality of energy storage devices (e.g., plurality of batteries or capacitors) that are arranged in parallel or series.

For ease of discussion, in an embodiment, the CEC 108 includes a single capacitor. In such an embodiment, the switchable lens 104 exhibits a capacitance $C_1$ and the capacitor of the CEC 108 exhibits a capacitance $C_2$. Without using the TEC 110, the switchable lens 104 can discharge electrical energy into the CEC 108 until the switchable lens 104 and the capacitor of the CEC 108 exhibit the same voltage (e.g., the CEC 108 and switchable lens 104 are substantially in equilibrium). The energy stored in the switchable lens 104, $U_1$, and the energy stored in the capacitor of the CEC 108, $U_2$, are related to each other by the equation $U_1/U_2 = C_1/C_2$ when the CEC 108 and switchable lens 104 are in equilibrium. The equation $U_1/U_2 = C_1/C_2$ is an example of an electrical energy equilibrium between two components of the system 100 when the at least one TEC 110 is not used ("equilibrium equation"). It is noted that in other embodiments, the equilibrium equation can be different than $U_1/U_2 = C_1/C_2$. For example, the equilibrium equation can be different than $U_1/U_2 = C_1/C_2$ when the CEC 108 includes a battery, etc.

The TEC 110 is configured to transfer electrical energy between a first component of the ophthalmic device 102 (e.g., the switchable lens 104) and second component of the ophthalmic device 102 (e.g., the CEC 108) such that the electrical energy stored in the first component and the electrical energy stored in the second component is not described by the equilibrium equation. For example, the TEC 110 can cause more or less of the electrical energy to be transferred between the first and second component than if TEC 110 was not used (e.g., bypassed).

The TEC 110 can include any suitable electrical circuitry that is configured to transfer electrical energy between the first and second component of the system 100. For example, the TEC 110 can include at least one charge pump circuit, inductor-based switching power supply, a DC-to-DC converter, or another suitable device. In an embodiment, the TEC 110 can be configured to receive an input voltage and provide an output voltage that is different than the input voltage. For example, the output voltage can greater than the input voltage by a factor of 1.25, 1.33, 1.5, 1.75, 2, 3, 4, 5, 6, 7, 8, 9, 10, 15, 20, 25, 30, 35, 40, 45, or 50 including ranges with end points having of the provided factors. Increasing the output voltage relative to the input voltage increases the amount of electrical energy transferred from a first component to a second component of the ophthalmic device 102. In another example, the output voltage can be less than the input voltage by a factor of 0.9, 0.8, 0.7, 0.6, 0.5, 0.4, 0.3, 0.2, or 0.1, including ranges with end points having any of the provided factors. Decreasing the output voltage relative to the input voltage decreases the amount of electrical energy transferred from a first component to a second component of the ophthalmic device 102. In an embodiment, the TEC 110 can be configured to provide an output voltage that is at least 50 times greater than or 0.1 times less than the input voltage received thereby.

In an embodiment, the system 100 can include a plurality of TECs. For example, the system 100 can include at least one first TEC between a first and second component of the ophthalmic device 102 and at least one second TEC between a third and fourth component of the ophthalmic device 102. The first TEC can be different than or the same as the second TEC. In another example, the system 100 can include at least one first TEC between a first and second component of the ophthalmic device 102 and at least one second TEC between the second component and a third component of the ophthalmic device 102. In another example, the system 100 can include a plurality of TECs between a first and second component of the ophthalmic device 102 that are in parallel or series with each other. Each of the plurality of TECs can be configured to transfer different amounts of electrical energy from the first component to second component of the ophthalmic device 102.

As previously discussed, the TEC 110 can be coupled to and electrically positioned between the switchable lens 104 and the CEC 108. In an embodiment, the TEC 110 can be configured to transfer electrical energy from the first and second electrodes to the CEC 108 (e.g., discharge the switchable lens 104). For example, the TEC 110 can be configured to transfer more or less electrical energy from the first and second electrodes to the CEC 108 than if the TEC 110 is not used. For instance, the TEC 110 can controllably transfer a significant portion of or substantially all of the electrical energy stored between the first and second electrodes to the CEC 108. In an embodiment, the TEC 110 can be configured to transfer electrical energy from the CEC 108 to the first and second electrodes (e.g., recharge the switchable lens 104). For example, the TEC 110 can be configured to transfer more or less electrical energy from CEC 108 to the first and second electrodes than if the TEC 110 is not used. For instance, the TEC 110 can controllably transfer a significant portion of or substantially all of the electrical energy stored by the CEC 108 to the first and second electrodes.

The power source 106 is electrically coupled to the switchable lens 104. In particular, the power source 106 is electrically coupled to the first and second electrodes. The power source 106 can also be electrically coupled to one or more components of the system 100. For example, the power source 106 can be electrically coupled to the CEC 108, the TEC 110, the controller 112, the transceivers 114, or the one or more sensors 116. In an embodiment, the power source 106 can be omitted and electrical power can be provided by the switchable lens 104 or the CEC 108.

The power source 106 is distinct from the CEC 108. The power source 106 can include any device configured to provide electrical power to one or more components of the ophthalmic device 102. For example, the power source 106 can include at least one capacitor, at least one battery (e.g., microbattery), or at least one fuel cell. In another example, the power source 106 can include at least one energy harvester that is configured to generate electrical energy. For instance, the energy harvester can include a photovoltaic cell, photodiode, or piezoelectric. In another example, the power source 106 can include at least one energy harvester coupled to and configured to charge at least one battery or at least one capacitor.

In an embodiment, power source 106 can include at least one primary power source electrically coupled to at least one intermediate power source. The intermediate power source can be electrically coupled to the switchable lens 104. The primary power source can include at least one battery or at least one fuel cell and the intermediate power source can include at least one capacitor. The primary power source can be configured to provide electrical power to (e.g., charge) the intermediate power source. The primary power source of the intermediate power source can be configured to provide electrical power to one or more other components of the ophthalmic device 102.

The at least one ophthalmic device 102 can also include additional electrical circuitry configured to facilitate the operation of the ophthalmic device 102. For example, the ophthalmic device 102 can include at least one discharge electrical circuitry that is electrically coupled to the switchable lens 104 (e.g., discharge electrical circuitry 274 of FIG. 2). The discharge electrical circuitry can be configured to substantially completely discharge the switchable lens 104 after a portion of (e.g., substantially all of) the electrical energy stored in the switchable lens 104 is discharged into the CEC 108. In another example, the ophthalmic device 102 can include at least one bypass electrical circuitry (e.g., bypass electrical circuitry 280 of FIG. 2). The bypass electrical circuitry can be operably coupled to one or more components of the ophthalmic device 102. The bypass electrical circuitry can be configured and positioned to flow electrical energy at least partially around one or more components (e.g., the TEC 110) of the ophthalmic device 102.

As previously discussed, the ophthalmic device 102 (e.g., at least one of the first or second ophthalmic devices 102a, 102b) can include one or more sensors 116 configured to sense one or more characteristics. The first ophthalmic device 102a, the second ophthalmic device 102b, or both can include one or more sensors 116 that are the same or are different. In an embodiment, the sensors 116 can be configured to sense one or more characteristics that can be used to determine vergence rotation between a first eye and a second eye of an individual ("vergence rotation"), a distance from the ophthalmic device 102 to an object of interest ("apparent object distance"), or other suitable characteristic. The vergence rotation or apparent object distance can be used to determine when the ophthalmic device 102 should selectively change the focal length of the switchable lens 104. For example, the sensors 116 can include at least one photodetector that is configured to sense one or more electromagnetic signals. The photodetector can sense one or more changes in the electromagnetic signals that can be at least partially used to determine vergence rotation or apparent object distance. In another example, the sensors 116 can include two or more electrodes configured to sense one or more electromyography signals associated with (e.g., at least partially generated by) a ciliary muscle. The sensed electromyography signals can be at least partially used to determine vergence rotation or apparent object distance. In another example, the sensors 116 can include one or more accelerometers that are configured to sense one or more accelerations (e.g., movements, rotations) of the ophthalmic device 102. The accelerations can be at least partially used to determine vergence rotation or apparent object distance. In another example, the sensors 116 can include a magnetic field sensor configured to sense one or more identifiable magnetic fields. The identifiable magnetic fields can be generated by a device disposed in at least one eye of the individual, on the individual, or articles worn by the individual. Changes in the sensed identifiable magnetic fields can be at least partially used to determine vergence rotation or apparent object distance.

Additional examples of sensors that can be used to sense one or more characteristics that can be used to determine vergence rotation or apparent object distance are disclosed in U.S. patent application Ser. No. 14/807,719 filed on Jul. 23, 2015; U.S. patent application Ser. No. 14/807,756 filed on Jul. 23, 2015; and U.S. Patent Application Ser. No. 15/221,362 filed concurrently herewith, the disclosure of each of which are incorporated herein, in its entirety, by this reference.

In an embodiment, the sensors 116 can be configured to sense one or more characteristics of the ophthalmic device 102. For example, the sensors 116 can sense the electrical energy stored by the switchable lens 104, the power source 106, or the CEC 108. In an embodiment, the sensors 116 can sense the voltage of the switchable lens 104, the power source 106, or the CEC 108. In an embodiment, the sensors 116 can sense the electrical current flowing between one or more components of the ophthalmic device 102. For example, the sensors 116 can include a microelectromechanical ("MEMS") voltmeter, MEMS multimeter, or another suitable sensor.

In an embodiment, the sensors 116 can be configured to output one or more sensing signals therefrom. The sensing signals can include the characteristics sensed by the sensors 116 encoded therein. The sensors 116 can output the sensing signals to one or more components of the system 100, such as the controller 112.

In an embodiment, the ophthalmic device 102 can include one or more physiological sensors (not shown). For example, the physiological sensors can be disposed in or on any portion of the ophthalmic device 102 (e.g., the frame 1005 of FIG. 10A, at least one of the haptics 1007 of FIG. 10B). The physiological sensors can be configured to sense one or more physiological characteristics. The physiological sensors can include a glucose sensor, a heart rate sensor, a pulse oximeter, a temperature sensor, a moisture sensor, or another suitable physiological sensor. The physiological sensors can be configured to output one or more physiological signals responsive to sensing one or more physiological characteristics. For example, the physiological sensors can transmit (e.g., via transmitter 114) the physiological signals to the controller 112 or to a device remote from the ophthalmic device 100. For example, the physiological sensor can transmit the physiological signals to an implanted or implantable device, a wearable device (e.g., insulin pump), or a computer or network that includes patient records.

The controller 112 can be communicably coupled to one or more components of the system 100 (e.g., one or more components of the first or second ophthalmic device 102a, 102b). The controller 112 can include control electrical circuitry configured to at least partially control the operation of the one or more components of the system 100 to which the controller 112 is communicably coupled. For example, the controller 112 can include memory storage medium 118 and at least one processor 120 operably coupled to the memory storage medium 118. In an embodiment, the controller 112 can direct the switchable lens 104 to allow electrical energy to be removed therefrom or added thereto to selectively change the focal length thereof. In an embodiment, the controller 112 can direct the power source 106 to provide electrical energy to one or more components of the ophthalmic device 102 (e.g., the switchable lens 104) or receive electrical energy from one or more components of the ophthalmic device 102 (e.g., from the CEC 108). In an embodiment, the controller 112 can direct the CEC 108 to receive or provide electrical energy to one or more components of the ophthalmic device 102. In an embodiment, the controller 112 can direct the TEC 110 to transfer electrical energy from a first component of the ophthalmic device 102 to a second component of the ophthalmic device 102.

The controller 112 can be communicably coupled to the sensors 116 such that the controller 112 receives the sensing signals outputted by the sensors 116. The processor 120 can analyze the sensing signals to determine vergence rotation or apparent object distance to determine whether the focal length of the switchable lens 104 should be selectively modified. The controller 112 can at least partially control the operation of one or more components of the system 100 responsive to the analysis by the processor 120. In an embodiment, the sensors 116 includes at least one accelerometer and the processor 120 can determine vergence rotation or apparent object distance when the accelerometers sense inward or outward rotation, etc. In an embodiment, the sensors 116 includes at least two electrodes and the processor 120 can determine vergence rotation or apparent object distance when the at least two electrodes sense one or more electromyography signals associated with the ciliary muscle. In an embodiment, the sensors 116 includes at least one magnetic field sensor and the processor 120 can determine vergence rotation or apparent object distance when the magnetic field sensor senses a change in an identifiable magnetic field. In an embodiment, the sensors 116 includes at least one photodetector and the processor 120 can determine vergence rotation or apparent object distance when the photodetector senses a change in an electromagnetic field that corresponds to vergence rotation between the eyes. In an embodiment, the sensors 116 can include a plurality of sensors and the processor 120 can determine vergence rotation or apparent object distance by comparing the sensing signals outputted by the plurality of sensors.

Additional embodiments disclosing how the controller 112 can determine vergence rotation or apparent object distance are described in U.S. patent application Ser. No. 14/807,719 filed on Jul. 23, 2015; U.S. patent application Ser. No. 14/807,756 filed on Jul. 23, 2015; and U.S. patent application Ser. No. 15/221,362, which were previously incorporated by reference herein.

The controller 112 can direct one or more components of the ophthalmic device 102 to transfer electrical energy therebetween responsive to determining vergence rotation or apparent object distance. For example, the controller 112 can direct the power source 106 to transfer electrical energy to the switchable lens 104 (e.g., bias the first and second electrodes), the switchable lens 104 to receive the electrical energy, or the TEC 110 to transfer electrical energy from the power source 106 to the switchable lens 104 responsive to determining vergence rotation or apparent object distance. In an embodiment, the controller 112 can direct the power source 106 to transfer electrical energy to the CEC 108, the CEC 108 to receive the electrical energy, or the TEC 110 to transfer electrical energy from the power source 106 to the CEC 108 responsive to determining vergence rotation or apparent object distance. In an embodiment, the controller 112 can direct the switchable lens 104 to transfer electrical energy to the power source 106, the power source 106 to receive the electrical energy, or the TEC 110 to transfer electrical energy from the switchable lens 104 to power source 106 responsive to determining vergence rotation or apparent object distance. In an embodiment, the controller 112 can direct the switchable lens 104 to transfer electrical energy to the CEC 108, the CEC 108 to receive the electrical energy, or the TEC 110 to transfer electrical energy from the switchable lens 104 to the CEC 108 responsive to determining vergence rotation or apparent object distance. In an embodiment, the controller 112 can direct the CEC 108 to transfer electrical energy to the switchable lens 104 (e.g., bias the first and second electrodes), the switchable lens 104 to receive the electrical energy, or the TEC 110 to transfer electrical energy from the CEC 108 to the switchable lens 104 responsive to determining vergence rotation or apparent object distance. In an embodiment, the controller 112 can direct the CEC 108 to transfer electrical energy to the power source 106, the power source 106 to receive the electrical energy, or the TEC 110 to transfer electrical energy from the CEC 108 to the power source 106 responsive to determining vergence rotation or apparent object distance.

In an embodiment, the controller 112 can be disposed in the first ophthalmic device 102a and remote from the second ophthalmic device 102b. In such an embodiment, the controller 112 can use the transceiver 114 of the first ophthalmic device 102a to communicate with and at least partially control the operation of the second ophthalmic device 102b. In an embodiment, the controller 112 is located remote from both of the first or second ophthalmic devices 102a, 102b (e.g., the controller 112 is incorporated into a mobile device computer, or network). In such an embodiment, the controller 112 can include a controller transceiver 122 that is communicably coupled to the transceiver 114 of the first or second ophthalmic devices 102a, 102b. As such, the controller 112 can used the controller transceiver 122 to receive the one or more sensing signals and at least partially control the first and second ophthalmic devices 102a, 102b. In an embodiment, the controller 112 can include a plurality of controllers and each of the first and second ophthalmic devices 102a, 102b can include at least one of the plurality of controllers at least partially disposed therein. Each of the plurality of controllers can be communicably coupled together using the transceivers 114. In an embodiment, the system 100 includes only a single ophthalmic device and the controller 112 is at least partially disposed in or spaced from the single ophthalmic device.

In an embodiment, the controller 112 can be communicably coupled to or include a user interface 124 configured to provide information related to the system 100 to a user (e.g., medical professional) or the individual. For example, the user interface 124 can receive one or more information signals from the controller 112 (e.g., at least some of the sensing signals, a status of the system 100, etc.) and provide at least some of the information signals to the user or the individual. As such, the user interface 124 can include one or more output devices such as a screen, chime, or haptic indicator. The user interface 124 can also be configured to accept input from the user or individual using one or more input devices (e.g., keyboard, buttons, levers, switches, or dials). As such the user interface 124 can be configured to receive one or more of inputs, instructions, or programming and transmit the input, instructions, or programming. The user interface 124 can include a desktop computer, a laptop computer, a tablet computer, a cellular device (e.g., smart phone), a watch, or a remote control.

In an embodiment, the transceiver 114 can be configured to communicate with an entity without using the controller 112. The entity can include one or more of a computer, a mobile device, a network, another device implanted or implantable into the individual, a device that the individual can wear, etc. For example, the transceiver 114 can be configured to communicate with an insulin pump when the physiological sensors include a glucose sensor.

In an embodiment, at least a portion of the ophthalmic device 102 can be hermetically sealed. For example, at least one of the switchable lens 104, the power supply 106, the CEC 108, the TEC 110, the controller 112 (e.g., if the controller is disposed in the ophthalmic device 102), the transceiver 114, the sensor 116, the physiological sensors, etc. can be hermetically sealed within the ophthalmic device 102. For example, in one or more embodiments, the ophthalmic device 102 can be highly miniaturized, self-contained and can involve two or more components.

Figure 3:
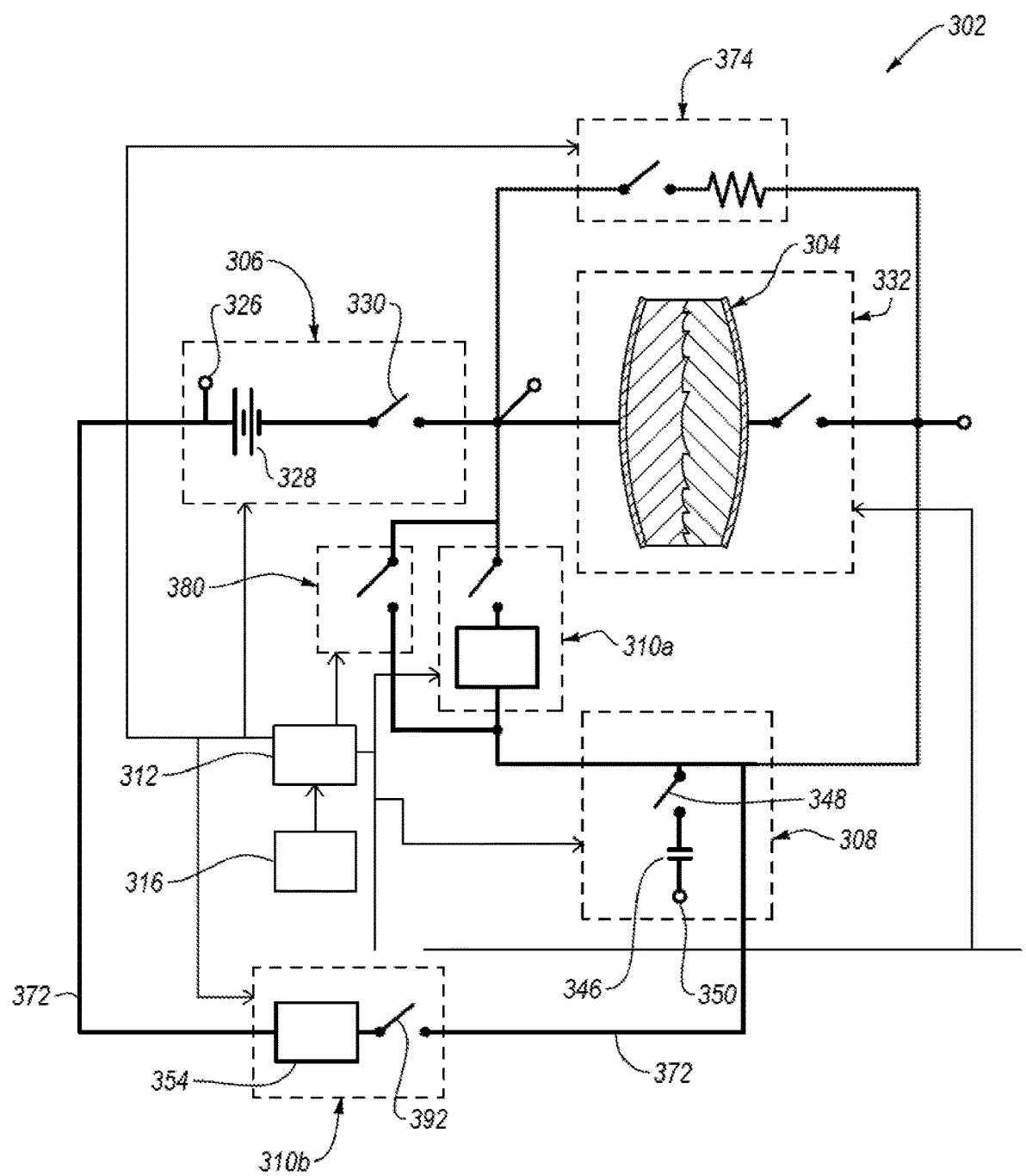
FIG. 3 is an electrical diagram illustrating at least some of the components of an ophthalmic device, according to an embodiment.
Figure 4:
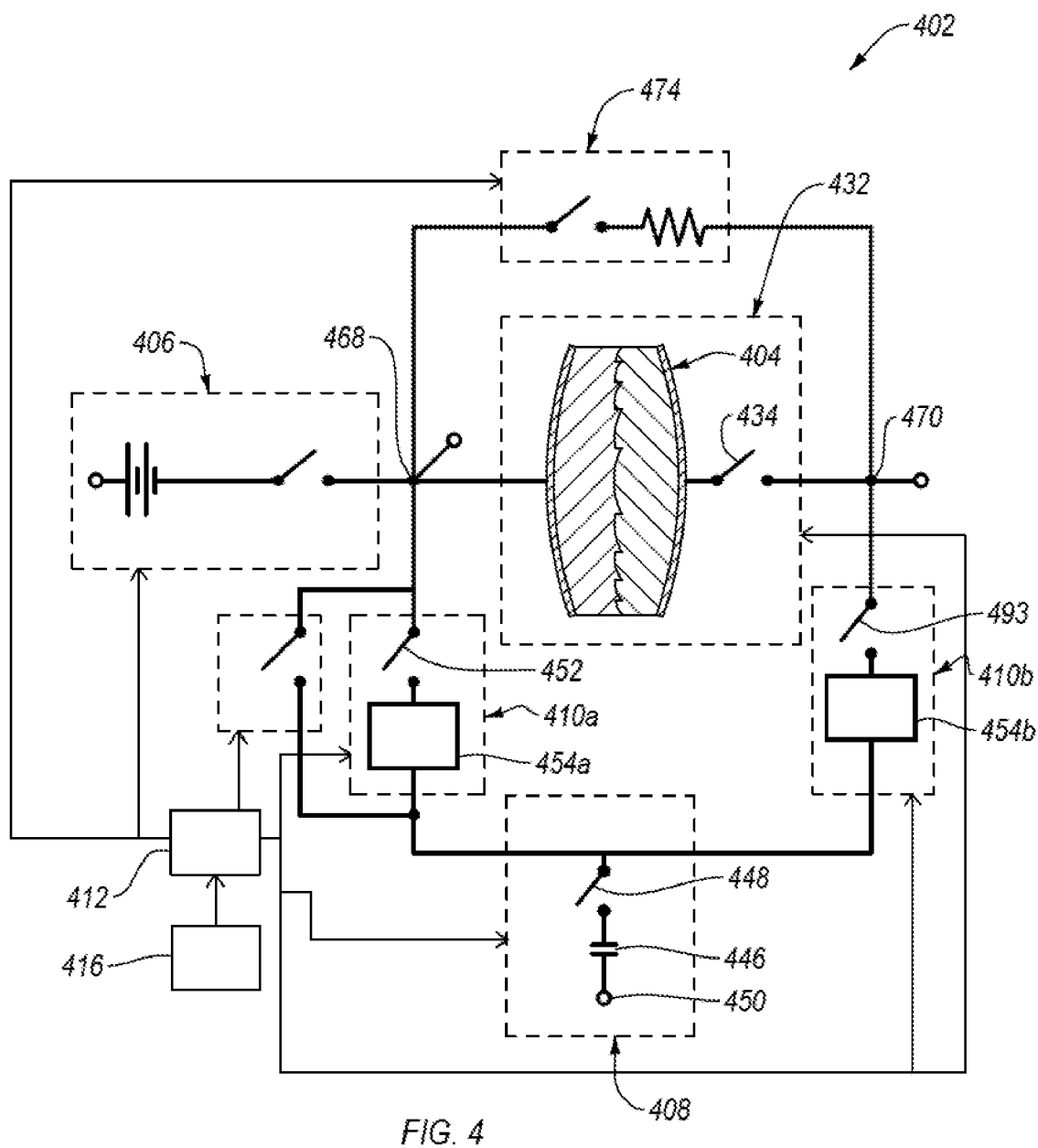
FIG. 4 is an electrical diagram illustrating at least some of the components of an ophthalmic device, according to an embodiment.

FIGS. 2, 3, and 4 are electrical diagrams illustrating at least some of the components of different ophthalmic devices, according to different embodiments. The electrical diagrams illustrated in FIGS. 2, 3, and 4 are provided for illustrative purposes only. It is understood that other circuits could be used instead of the circuits illustrated in FIGS. 2, 3, and 4. For example, the other circuits can be relatively more complex, relatively simpler, include more components, include fewer components, be arranged differently, or include additional electrical circuitry than the circuits illustrated in FIGS. 2, 3, and 4.

Except as otherwise described herein, the ophthalmic devices illustrated in FIGS. 2, 3, and 4 and their materials, components, or elements can be similar to or the same as the ophthalmic device 102 (FIG. 1) and its respective materials, components, or elements. The ophthalmic devices illustrated in FIGS. 2, 3, and 4 or their materials, components, or elements can be used in any of the system or ophthalmic device embodiments disclosed herein. For example, at least one material, component, or element of one of the ophthalmic devices illustrated in FIGS. 2, 3, and 4 can be used in another of the ophthalmic devices illustrated in FIGS. 2, 3, and 4.

The electrical diagrams illustrated in FIGS. 2, 3, and 4 include a plurality of terminals. For example, a terminal can include a conventional terminal (e.g., splice, hook, solder lug, tongue crimp, turret, clip, screw terminal, etc.), a similar electrical component, or a similar electrical connection that allows electricity to flow through the electrical diagrams, as described below. For example, a terminal can include a ground or at least one electrical connection to at least one other terminal, another portion of the electrical diagram, or at least one other component of the ophthalmic device.

The electrical diagrams illustrated in FIGS. 2, 3, and 4 include a plurality of switches. For example, a switch can include any electrical component or device that permits or restricts the flow of electrical energy to or from a device. For example, a switch can include a traditional switch (e.g., SPST, SPDT, DPDT, multipoint switch, etc.), a relay (e.g., thermal, solid state, etc.), a diode, a thyristor (e.g., TRIAC, DIAC, etc.), or another suitable device.

Referring to FIG. 2, the ophthalmic device 202 includes a power source 206. The power source 206 of the ophthalmic device 202 can include a first terminal 226, at least one battery 228, and at least one first switch 230. The battery 228 can include a DC voltage source, an AC voltage source, a single cell battery, a multi-cell battery, or a photocell. It is also understood that the battery 228 can be replaced with or used in conjunction with a capacitor, a fuel cell, or another suitable electrical energy source. The first switch 230 can be configured to selectively permit or restrict the flow of electrical energy from the power source 206.

The ophthalmic device 202 includes at least one lens electrical circuitry 232. The lens electrical circuitry 232 can include a switchable lens 204 and a second switch 234. The switchable lens 204 can include at least one layer 236 having a first outer surface 238 and a second outer surface 240. The switchable lens 204 can include a first electrode 242 adjacent to the first outer surface 238 and a second electrodes 244 adjacent the second outer surface 240. The switchable lens 204 can include any of the switchable lenses disclosed herein. For example, in the illustrated embodiment, the switchable lens 104 can include a switchable diffractive lens. The second switch 234 can be configured to selectively permit or restrict the flow of electrical energy into and from the switchable lens 204.

The ophthalmic device 202 can include at least one CEC 208. The CEC 208 can include a device that is configured to receive or provide electrical energy to at least one component of the ophthalmic device 202 (e.g., the switchable lens 204). For example, the CEC 208 can include at least one capacitor 246. In an embodiment, the CEC 208 can include a rechargeable battery. In an embodiment, the CEC 208 can include a plurality of capacitors 246 or batteries that are in series or parallel with each other. In an embodiment, the CEC 208 can include at least one capacitor 246 and at least one rechargeable battery that are in series or parallel with each other.

The CEC 208 can also include at least one third switch 248. The third switch 248 can be configured to selectively permit or restrict the flow of electrical energy to and from the CEC 208. For example, the third switch 248 can be configured and electrically positioned to selectively permit or restrict the flow of electrical energy to and from the capacitor 246. The third switch 248 can be in series with or parallel to the capacitor 246. The CEC 208 can also include at least one second terminal 250 that is in series or parallel to the capacitor 246 and in series with or parallel to the third switch 248.

Figure 2A:
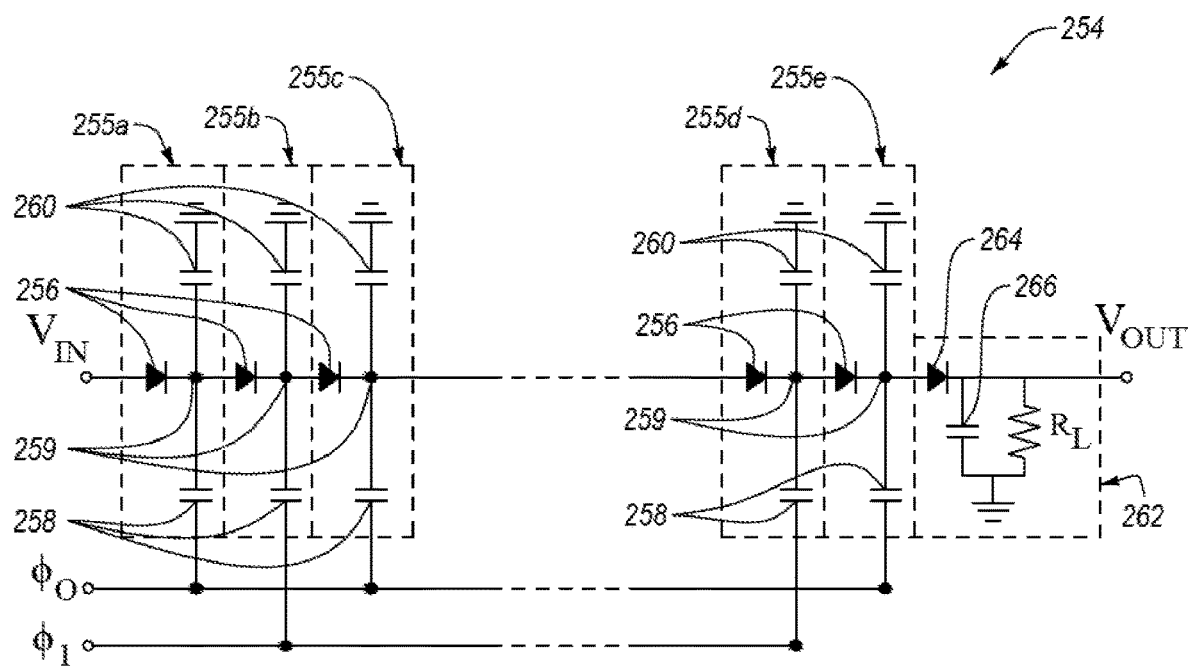
FIG. 2A is an electrical diagram of the charging pump circuit, according to an embodiment.

A TEC 210 is provided that can include at least one fourth switch 252 and at least one CPC 254. FIG. 2A is an electrical diagram of the CPC 254, according to an embodiment. In particular, the CPC 254 illustrated in FIG. 2A is an example of a Dickson CPC. However, it is understood that the CPC 254 can include any suitable CPC, such as a single stage CPC, a multiple stage CPC, a Dickson CPC with MOS diodes or switches, a Cockcroft-Walton voltage multiplier, a static charge transfer switches CPC, a complementary metal-oxide-semiconductor (CMOS) CPC, a charge pump cell circuit, a bootstrap CPC, a double CPC, a latched CPC, a series-parallel CPC, a CPC with adaptive steps, another suitable CPC, or combinations thereof. The fourth switch 252 can be configured to selectively permit or restrict the flow of electrical energy through the CPC 254. In an embodiment, the CPC 254 can be replaced or used in conjunction with a inductor-based switching power supply, a DC to DC converter, or other suitable voltage multiplier.

Referring to FIG. 2A, the CPC 254 includes N stages 255, where N is an integer. Each stage includes a diode 256, a CPC capacitor 258, a CPC node 259, and an imaginary stray capacitor 260 that is used to represent the stray capacitance inherently present in the CPC 254. It is noted that the diodes 256 can be replaced with any of the switched disclosed herein. In an embodiment, the CPC 354 includes a first stage 255a, a second stage 255b, a third stage 255c, a (N−1) stage 255d, and an N stage 255e. The CPC 254 also includes an input voltage $V_{IN}$ that is applied to the first stage 255a. The CPC 254 also includes two pumping clocks $\phi_0$ and $\phi_1$, both of which are anti-phase and exhibit a voltage of $V_\phi$ (not shown). In an embodiment, the voltage $V_{99}$ can be equal to the input voltage $V_{IN}$ and originate from the same source as the input voltage $V_{IN}$. The illustrated CPC 254 has also been modified to include an output stage 262 to accommodate a load at the output. The output stage 262 includes an output diode 264, and output capacitor 266 having an output capacitance, and a ripple load $R_L$. The CPC 254 is configured to provide an output voltage $V_{OUT}$.

In operation, the CPC 254 operates by pumping a charge along the diode chain as each CPC capacitor 258 is successively charged and discharged. In a first step, the clock phase $\phi_0$ is low and the clock phase $\phi_1$ is high. During the first step, the diode 256 of the first stage 255a allows electricity to flow until the voltage of the node 259 of the first stage 255a equals $(V_{IN}-V_D)$, where $V_D$ is the voltage drop across the diodes 256. In a second step, $\phi_0$ is high and $\phi_1$ is low. During the second step, the voltage of the node 259 of the first stage 255a equals $(V_\phi+V_{IN}-V_D)$. The diode 256 of the second stage 255b conducts electricity until the node 259 of the second stage 255b equals $(V_\phi+V_{IN}-2V_D)$. In a third step, the clock phase $\phi_0$ is low and the clock phase $\phi_1$ is high. During the third step, the diode 256 of the first stage 255a allows electricity to flow until the voltage of the node 259 of the first stage 255a equals $(V_{IN}-V_D)$. Similarly, during the third step, the diode 256 of the third stage 255c allows electricity to flow until the voltage of the node 259 of the third stage 255c equals $(V_{IN}+2V_\phi-3V_D)$. Continuing to follow the charge along the diode chain results in an estimated output voltage $V_{OUT}$ that equals $(V_{IN}+N*(V_\phi-V_D)-V_D)$. However, the output voltage $V_{OUT}$ can be smaller than the estimated output voltage due to the effects of the stray capacitors 260, the output capacitor 266, and the ripple load $R_L$.

Referring back to FIG. 2, the TEC 210 is electrically positioned between and coupled to the lens electrical circuitry 232 and the CEC 208. As such, the TEC 210 is configured to transfer electrical energy stored between the first and second electrodes 242, 244 to the CEC 208. As will be discussed in more detail in FIGS. 3 and 4, the ophthalmic device 202 can include a plurality of TECs 210 or the TEC 210 can be electrically positioned between different components of the ophthalmic device 202.

In an embodiment, the TEC 210 can include a plurality of CPCs that are arranged in series or parallel. Each of the CPC's can be configured to output different output voltages $V_{OUT}$. For example, each of the CPC's can include different number of stages. In such an embodiment, the controller 212 can controllably activate different ones of the CPC's to control the amount of electrical energy transferred from a first component of the ophthalmic device (e.g., the switchable lens 204) to a second device of the ophthalmic device 202 (e.g., the CEC 208). In another embodiment, the TEC 210 can include a plurality of inductor-based switching power supplies, DC to DC converters, etc. that are arranged in series or parallel.

The ophthalmic device 202 can include a first node 268 and a second node 270. In an embodiment, the first and second nodes 268, 270 can be a conductor connection that couples the power source 206, the lens electrical circuitry 232, the CEC 208, and the TEC 210 together. For example, the power source 206, the lens electrical circuitry 232, and the TEC 210 can include electrical conductors 272 (e.g., wires) extending therefrom that are connected together at the first node 268. Similarly, the lens electrical circuitry 232 and the CEC 208 can include electrical conductors 272 extending therefrom that are connected together at the second node 270. In an embodiment, the first node 268 and the second node 270 can also include a third terminal 273 and a fourth terminal 275 extending therefrom, respectively. In an embodiment, the lens electrical circuitry 232, the CEC 208, and the TEC 210 are connected together using additional nodes (not shown).

In an embodiment, the ophthalmic device 202 also includes at least one discharge electrical circuitry 274. The discharge electrical circuitry 274 can be electrically coupled to the lens electrical circuitry 232 (e.g., the switchable lens 204) such that the discharge electrical circuitry 274 can completely discharge the electrical energy stored between the first and second electrodes 242, 244. For example, at least some of the electrical energy stored between the first and second electrodes 242, 244 can remain after the switchable lens 204 discharges at least some (e.g., substantially all) of the electrical energy to the CEC 208. The discharge electrical circuitry 274 can include a fifth switch 276 and a resistor 278. The resistor 278 can be configured to dissipate electrical energy stored in the switchable lens 204 as heat and the fifth switch 276 can be configured to selectively permit or restrict the flow of electrical energy across the resistor 278. The discharge electrical circuitry 274 can be electrically coupled to the lens electrical circuitry 232 using the first and second nodes 268, 270.

In an embodiment, the ophthalmic device 202 also includes at least one bypass electrical circuitry 280. The bypass electrical circuitry 280 is positioned and configured to enable electrical energy to flow at least partially around one or more components of the ophthalmic device 202. For example, in the illustrated embodiment, the bypass electrical circuitry 280 is positioned and configured to enable electrical energy to bypass the TEC 210. For instance, the bypass electrical circuitry 280 can be configured to enable electrical energy to transfer between the lens electrical circuitry 232 and the CEC 208 such that the amount of electrical energy stored in the switchable lens 204 and the capacitor 246 is define by the equilibrium equation discussed above.

The bypass electrical circuitry 280 can include a sixth switch 282 and electrical conductors 272 extending therefrom. In an embodiment, the electrical conductors 272 extending from the bypass electrical circuitry 280 can be coupled to the electrical conductors 272 extending from the TEC 210 using a third node 284 and a fourth node 286. The third node 284 can be coupled to the electrical conductor 272 extending from an input 288 of the TEC 210 (e.g., positioned at or near the input 288) and the fourth node 286 can be coupled to the electrical conductor 272 extending from an output 290 of the TEC 210 (e.g., positioned at or near the output 290). The sixth switch 282 can be configured to allow electrical energy to flow through the bypass electrical circuitry 280 thereby bypassing the TEC 210. The bypass electrical circuitry 280 can be similar positioned and configured to bypass other components of the ophthalmic device 202.

In an embodiment, the bypass electrical circuitry 280 is positioned and configured to bypass only a portion of the CPC 254. For example, referring to FIG. 2A, at least one of the electrical conductors 272 extending from the bypass electrical circuitry 280 can be coupled to the CPC 254 before or after the diode 256 of the first, second, third, (N−1)th, Nth, or output stage 255a, 255b, 255c, 255d, 255e, 262. In such an example, the bypass electrical circuitry 280, when the sixth switch 282 is closed, essentially decreases the number of stages on the CPC 254 from N stages to a single stage, two stages, three stages, (N−1) stages, etc.

The ophthalmic device 202 can include or be communicably coupled to at least one controller 212. The controller 212 can be communicably coupled to and configured to at least partially control the operation of the power source 206, the lens electrical circuitry 232, the CEC 208, the TEC 210, the discharge electrical circuitry 274, and the bypass electrical circuitry 280. For example, the controller 212 can be configured to transmit one or more command signals 291 that direct the power source 206, the lens electrical circuitry 232, the CEC 208, the TEC 210, the discharge electrical circuitry 274, and the bypass electrical circuitry 280 to operate. The controller 212 can also be communicably coupled to one or more sensors 216. The sensors 216 can be configured to transmit one or more sensing signals to the controller 212 and the controller 212 can analyze the sensing signals to determine when the switchable lens 204 selectively switches a focal length thereof. The controller 212 can direct the one or more components of the ophthalmic device 202 to selectively change the amount of electrical energy stored between the first and second electrodes 242, 244 when the controller 212 determines that the focal length of the switchable lens 204 is to be selectively switched.

In an embodiment, the controller 212 can determine that electrical energy is to be provided to the switchable lens 204 from the power source 206. In such an embodiment, the controller 212 can direct the first and second switches 230, 234 to close, thereby allowing electrical energy to transfer from the power source 206 to the switchable lens 204 (e.g., biasing the first and second electrodes 242, 244). The first and fourth terminals 226, 275 can also be configured to enable electrical energy to flow from the power source 206 to the switchable lens 204 (e.g., the first and fourth terminals 226, 275 are connected together or the ground). The controller 212 can direct the power source 206 to provide electrical power to the switchable lens 204, for example, when the switchable lens 204 is first charged (e.g., the switchable lens 204 and the CEC 208 are not charged), the total electrical energy stored in the switchable lens 204 and the CEC 208 is insufficient, or the CEC 208 is unable to provide sufficient electrical energy to the switchable lens 204.

In an embodiment, the controller 212 can determine that electrical energy is to be removed from the switchable lens 204. For example, the controller 212 can direct the second, third, and fourth switches 234, 248, 252 to close, thereby transferring electrical energy from the switchable lens 204 (e.g., the first and second electrodes 242, 244) to the CEC 208 (e.g., the capacitor 246). Closing the fourth switch 252 allows the TEC 210 to increase or decrease the amount of electrical energy transferred between the first and second electrodes 242, 244 and the CEC 208 than if the TEC 210 was not used. In an embodiment, the controller 212 can direct the second, third, and sixth switches 234, 248, 282 to close thereby, transferring electrical energy from the switchable lens 204 to the CEC 208 without using the TEC 210 or using only a portion of the TEC 210. In any of the above examples, the second and fourth terminals 250, 275 can be configured to allow electrical energy to be transferred from the first and second electrodes 242, 244 to the capacitor 246 (e.g., the second and fourth terminals 250, 275 are connected together or the ground).

In any of the embodiments disclosed herein involving electrical energy flowing through the TEC 210 or the CPC 254, the controller 212 can direct the TEC 210 or CPC 254 to allow the electrical energy to flow therethrough. For example, the CPC 254 can include at least one switch (e.g., the CPC 254 can include switches instead of diodes 256) and the controller 212 can direct the at least one switch to selectively open and close. In another example, the controller 212 can selectively change the clock signal between the two pumping clocks $\phi_0$ and $\phi_1$.

In an embodiment, the controller 212 can determine that electrical energy is to be provided to the switchable lens 204 from the CEC 208. In such an embodiment, the controller 212 can direct the second and third switches 234, 248 to close, thereby transferring electrical energy from the CEC 208 (e.g., the capacitor 246) to the switchable lens 204 and biasing the first and second electrodes 242, 244. As such, the controller 212 can direct the CEC 208 to charge or recharge the switchable lens 204. In such an embodiment, the second and third terminals 250, 273 can be configured to allow electrical energy to be transferred from the capacitor 246 to the first and second electrodes 242, 244 (e.g., the second and third terminals 250, 273 are connected together or the ground).

In an embodiment, the controller 212 can determine that electrical energy is to be removed from the switchable lens 204 before or after at least some of the electrical energy stored between the first and second electrodes 242, 244 was transferred to the CEC 208. In such an embodiment, the controller 212 can direct the second and fifth switches 234, 276 to close, thereby allowing the switchable lens 204 to completely discharge the electrical energy stored therein via the discharge electrical circuitry 274.

In an embodiment, the controller 212 can direct the power source 206 to transfer electrical energy to the CEC 208 (e.g., to the capacitor 246). In such an embodiment, the controller 212 can direct the first switch 230, the third switch 248, and at least one of the fourth or sixth switches 252, 282 to close. For example, the controller 212 can direct the power source 206 to transfer electrical energy to the CEC 208 because the capacitor 246 can charge the first and second electrodes 242, 244 faster than the battery 228. In such an embodiment, the first and second terminals 226, 250 are configured to allow electrical energy to be transferred between the power source 206 and the CEC 208 (e.g., the first and second terminals 226, 250 are connected together or to the ground).

Referring to FIG. 3, the ophthalmic device 302 is substantially similar to the ophthalmic device 202 (FIG. 2). For example, the ophthalmic device 302 can include a power source 306, a lens electrical circuitry 332, a CEC 308, a discharge electrical circuitry 374, a controller 312, and one or more sensors 316. However, the CEC 308 is directly coupled to and configured to recharge the power supply 306. For example, the ophthalmic device 302 can also include a second TEC 310b electrically positioned between the CEC 308 and the power supply 306 that is configured to transfer more or less electrical energy between the CEC 308 and the power supply 306 than if the second TEC 310b is omitted.

The ophthalmic device 302 can also include a first TEC 310a. The first TEC 310a can be the same as or substantially similar to the TEC 210 (FIG. 2). For example, the first TEC 310a can be electrically positioned between and coupled to the lens electrical circuitry 332 and the CEC 308. The first TEC 310a can be configured to increase or decrease the amount of electrical energy transferred between switchable lens 304 and the CEC 308 than if the first TEC 310a is omitted. In an embodiment, the first TEC 310a can be omitted or at least partially bypassed using the bypass electrical circuitry 380.

As previously discussed, the power source 306 is electrically coupled to the CEC 308. For example, the CEC 308 can include an electrical conductor 372 extending that is in series with or parallel to the capacitor 346, the third switch 348, or the second terminal 350. Similarly, the power source 306 can include an electrical conductor 372 extending therefrom that is in series with or parallel to the battery 328 or the first terminal 326.

In an embodiment, the ophthalmic device 302 can include a second TEC 310b coupled to the power source 306 and the CEC 308. For example, the power source 306 and the CEC 308 can include electrical conductors 372 extending therefrom that are electrically coupled to the second TEC 310b. The second TEC 310b can be configured to transfer electrical energy from the CEC 308 to the power source 306. As such, the second TEC 310b can include a seventh switch 392 and a CPC 354. The seventh switch 392 can be configured to permit the flow of electrical energy through the second TEC 310b when the first, third, and seventh switches 330, 348, 392 are closed. The CPC 354 can be configured to decrease or increase the amount of electrical energy transferred from the CEC 308 to the power source 306 than if the second TEC 310b was not present. As such, the second TEC 310b can facilitate charging or recharging the power source 306 (e.g., charging or recharging the battery 328) by the CEC 308. In an embodiment, the second TEC 310b can be at least partially omitted (e.g., the CPC 354 is omitted and the seventh switch 392 remains) or the second TEC 310b can be at least partially bypassed by a second bypass electrical circuitry (not shown).

In an embodiment, the controller 312 can direct the CEC 308, the second TEC 310b, or the power source 306 to transfer electrical energy from the CEC 308 to the power source 306. For example, the controller 312 can direct the first, third and seventh switches 330, 348, 392 to close thereby allowing electrical energy to flow from the CEC 308 to the power source 306. The controller 312 can direct the CEC 308 or the second TEC 310b to transfer electrical energy from the CEC 308 to the power source 306 when the electrical energy stored in the power source 306 is relatively low or the electrical energy stored in the CEC 308 is relatively high.

Referring to FIG. 4, the ophthalmic device 402 is substantially similar to the ophthalmic device 202 (FIG. 2). For example, the ophthalmic device 402 can include a power source 406, a lens electrical circuitry 432, a CEC 408, a discharge electrical circuitry 474, a controller 412, and one or more sensors 416. However, the ophthalmic device 402 includes a first TEC 410a and a second TEC 410b electrically positioned between the switchable lens 404 and the CEC 408.

The first TEC 410a can be similar to or the same as the TEC 210 (FIG. 2). For example, the first TEC 410a can include a fourth switch 452 and a first CPC 454a. The second TEC 410b can also be similar to or the same as the TEC 210 (FIG. 2). For example, the second TEC 410b can include an eighth switch 493 and a second CPC 454b. In an embodiment, the first and second TECs 410a, 410b can be electrically positioned between the lens electrical circuitry 432 and the CEC 408. For example, the first TEC 410a can be directly electrically coupled to the first node 468 and the second TEC 410b can be directly electrically coupled to the second node 470.

In an embodiment, the first and second TECs 410a, 410b can be configured to transfer electrical energy between the lens electrical circuitry 432 and the CEC 408. For example, the first TEC 410a can be configured to transfer at least some of (e.g., a significant portion of, substantially all of) the electrical energy stored in the switchable lens 404 to the CEC 408. The first TEC 410a can transfer the electrical energy from the switchable lens 404 to the CEC 408 when the second switch 434 of the lens electrical circuitry 432, the third switch 448, and the fourth switch 452 are closed. In another example, the second TEC 410*b* can be configured to transfer at least some of (e.g., a significant portion of, substantially all of) the electrical energy stored in the CEC 408 to the switchable lens 404. The second TEC 410*b* can transfer the electrical energy from the CEC 408 to the switchable lens 404 when the second switch 434 and the eighth switch 493 are closed.

FIGS. 5-8 are flow diagrams of methods 500, 600, 700, 800, respectively, of modifying at least one optical property of at least one switchable lens of any of the ophthalmic devices disclosed herein, according to various embodiments. In an embodiment, some of the acts of methods 500, 600, 700, 800 can be split into a plurality of acts, some of the acts can be combined into a single act, and some acts can be omitted. Also, it is understood that additional acts can be added to the methods 500, 600, 700, 800, such as acts from different methods. Except as otherwise disclosed herein, the acts of methods 500, 600, 700, 800 can be used with any of the ophthalmic devices and systems disclosed herein.

Figure 5:
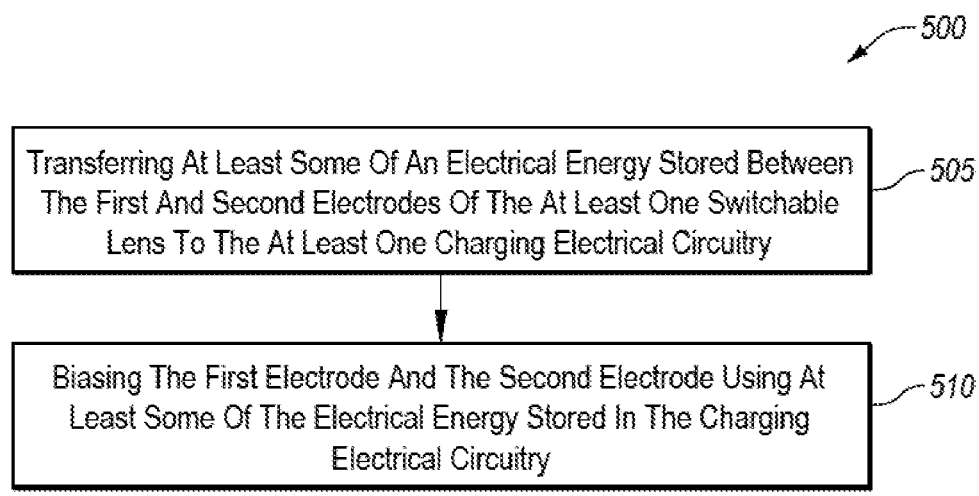
FIGS. 5-8 are flow diagrams of methods of modifying at least one optical property of at least one switchable lens of any of the ophthalmic devices disclosed herein, according to various embodiments.

Referring to FIG. 5, the method 500 includes act 505 of transferring at least some of an electrical energy stored between the first and second electrodes of the at least one switchable lens to the at least one CEC and act 510 of biasing the first electrode and the second electrode using at least some of the electrical energy stored in the CEC. Act 510 can be performed before or after act 505. For example, act 505 can include transferring a significant portion of or substantially all of the electrical energy stored between the first and second electrodes to the CEC.

In an embodiment, act 505 can include changing at least one optical property of the switchable lens. For example, act 505 can include changing at least one of an index of refraction, transmissivity, spectral filtering, or phase shift of the at least one electro-optical material of the switchable lens. For example, act 505 can include changing the optical property from a first optical property (e.g., a first index of refraction, a first transmissivity, a first spectral filtering, or a first phase shift) to a second optical property (e.g., a second index of refraction, a second transmissivity, a second spectral filtering, or a second phase shift) that is different than the first optical property. Similarly, act 505 can include changing the optical property to at least one additional optical property that is different than the first and second optical properties.

In an embodiment, act 505 can include changing a focal length of the at least one switchable lens from a first focal length to a second focal length. For example, changing a focal length of the at least one switchable lens can include changing an index of refraction, transmissivity, spectral filtering, or phase shift of the at least one electro-optical material of the switchable lens. In an embodiment, act 505 can include changing the focal length of the at least one lens to at least one additional focal length that is between the first focal length and the second focal length. In an embodiment, changing a focal length of the at least one switchable lens can include controllably or selectively changing the focal length of the switchable lens.

In an embodiment, act 505 can include transferring the electrical energy stored between the first and second electrodes to the CEC via at least one TEC. Transferring the electrical energy stored between the first and second electrodes to the CEC via at least one TEC can include transferring more or less of the electrical energy from the first and second electrodes to the CEC than if the TEC is not present. For example, transferring the electrical energy stored between the first and second electrodes to the CEC via at least one TEC includes transferring a significant portion of, substantially all of, or all of the electrical energy stored between the first and second electrodes to the CEC.

In an embodiment, act 505 can include, with the at least one controller, directing the lens electrical circuitry and the CEC to transfer the electrical energy stored between the first and second electrodes to the CEC. For example, directing the lens electrical circuitry and the CEC to transfer the electrical energy stored between the first and second electrodes to the CEC can include, with the controller, directing the second switch of the lens electrical circuitry (e.g., second switch 234 of FIG. 2) and the third switch of the CEC (e.g., third switch 248 of FIG. 2) to close. In an embodiment, transferring at least some of the electrical energy stored between the first and second electrodes to the CEC can include, with the at least one controller, directing the TEC to transfer at least some of the electrical energy stored between the first electrode and the second electrode of the switchable lens to the CEC. For example, directing the TEC to transfer at least some of the electrical energy stored between the first electrode and the second electrode of the switchable lens to the CEC includes, with the controller, directing the fourth switch of the TEC (e.g., fourth switch 252 of FIG. 2) to close or controlling one or more components of a CPC (e.g., controlling the pumping clocks).

As discussed above, the method 500 includes act 510 of biasing the first electrode and the second electrode using at least some of the electrical energy stored in the CEC. Act 510 can be performed before or after act 505. In an embodiment, act 510 can include biasing the first and second electrodes using a significant portion of or substantially all of the electrical energy stored in the CEC. However, it is noted that act 510 can be omitted from method 510.

In an embodiment, act 510 can include transferring at least some of the electrical energy from the CEC to the first and second electrodes using at least one TEC. Transferring at least some of the electrical energy from the CEC to the first and second electrodes using at least one TEC can include transferring more or less of the electrical energy from the CEC to the first and second electrodes than if the TEC is not used. For example, transferring at least some of the electrical energy from the CEC to the first and second electrodes using at least one TEC can include transferring a significant portion of or substantially all of the electrical energy stored between the first and second electrodes to the CEC.

In an embodiment, act 510 can further include, with at least one controller, directing the CEC to bias the first and second electrodes using at least some of the electrical energy stored therein. For example, directing the CEC to bias the first and second electrodes can include, with the controller, directing the second switch of the lens electrical circuitry (e.g., second switch 234 of FIG. 2) and the third switch of the CEC (e.g., third switch 248 of FIG. 2) to close. In an embodiment, act 510 can further include, with at least one controller, directing the TEC to transfer at least some of the electrical energy from the CEC to the first and second electrodes. For example, directing the TEC to transfer at least some of the electrical energy from the CEC to the first and second electrodes can include, with the controller, directing the fourth switch of the TEC (e.g., fourth switch 252 of FIG. 2) to close or controlling one or more components of a CPC (e.g., controlling the pumping clocks).

Figure 6:
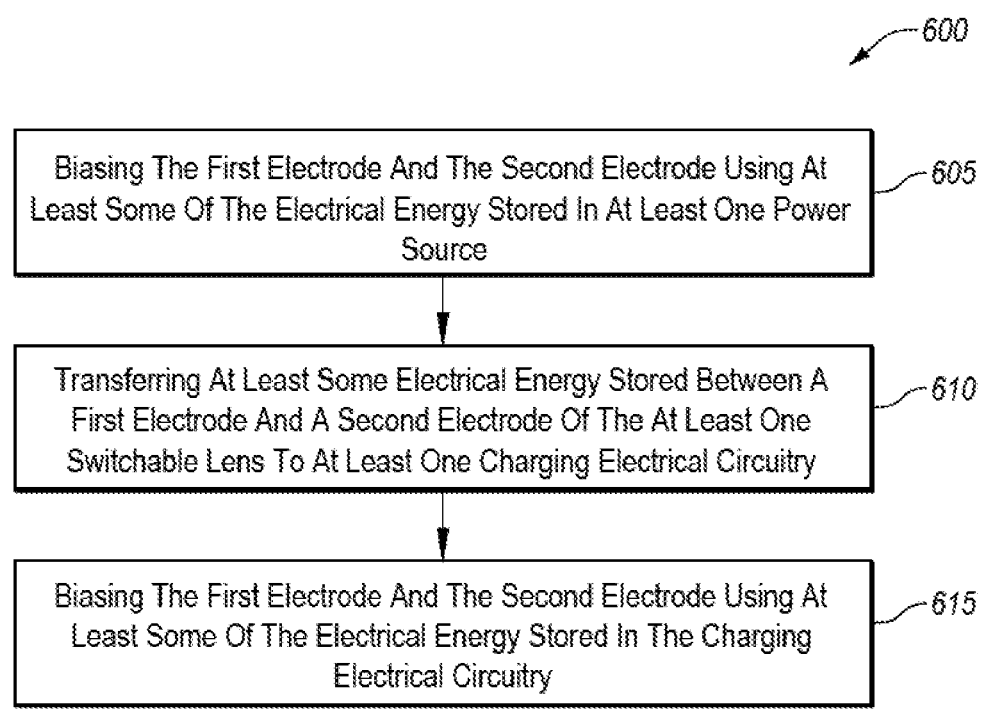

Referring to FIG. 6, the method 600 includes act 605 of biasing the first electrode and the second electrode using at least some of the electrical energy stored in at least one power source. For example, biasing the first and second electrodes can include initially providing electrical energy to the first and second electrodes (e.g., the first and second electrodes and the CEC have no electrical energy stored therein). In another example, biasing the first and second electrodes can include providing power via the power source to the first and second electrodes to increase the electrical energy stored in the CEC and between the first and second electrodes. In another example, biasing the first and second electrodes can include providing power via the power source to the first and second electrodes to recoup at least some of the electrical energy lost during the operation of the ophthalmic device. For instance, electrical energy can be lost during the operation of the ophthalmic device due to the internal resistance of the ophthalmic device, stray capacitance, the discharge electrical circuitry, etc. In an embodiment, act 605 can further include, with at least one controller, directing the power source to bias the first and second electrodes using at least some of the electrical energy stored therein.

The method 600 further includes acts 610 and 615. Act 610 includes transferring at least some electrical energy stored between a first electrode and a second electrode of the at least one switchable lens to at least one CEC. Act 615 includes biasing the first electrode and the second electrode using at least some of the electrical energy stored in the CEC. As such, acts 610 and 615 can be the same as or similar to acts 505 and 510, respectively, of method 500 (FIG. 5). Acts 610 or 615 can be performed before or after act 615.

Figure 7:
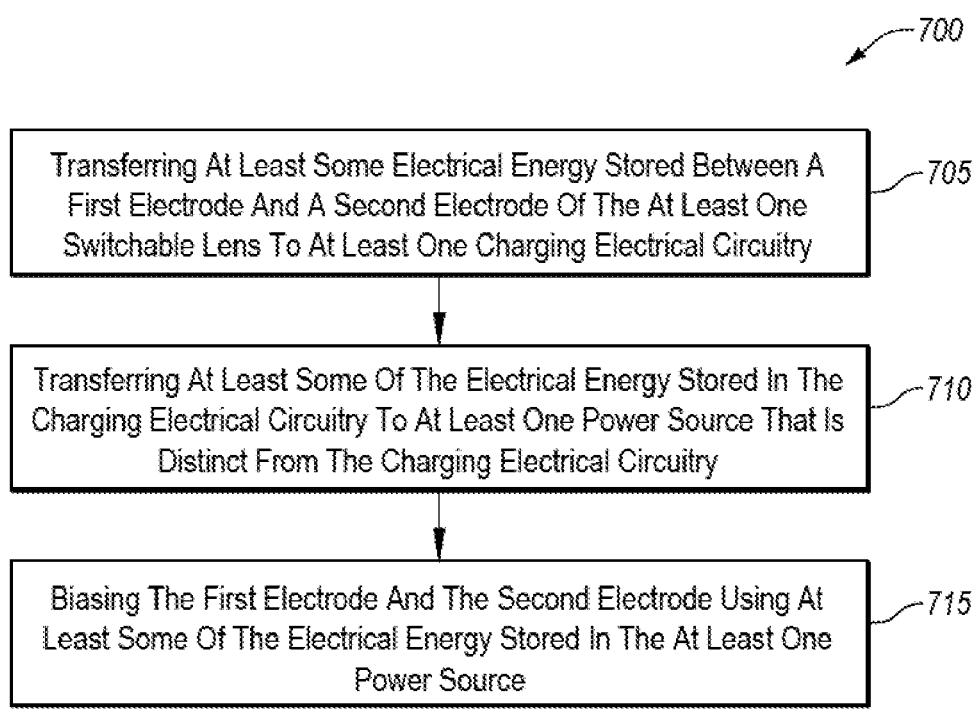

Referring to FIG. 7, the method include act 705 of transferring at least some electrical energy stored between a first electrode and a second electrode of the at least one switchable lens to at least one CEC. As such, act 705 can be substantially similar to or the same as act 505 of method 500 (FIG. 5).

The method 700 also includes act 710 of transferring at least some of the electrical energy stored in the CEC to at least one power source that is distinct from the CEC. For example, transferring at least some of the electrical energy stored in the CEC to the power source can include transferring a significant portion or substantially all of the electrical energy stored in the CEC to the power source. The CEC can transfer electrical energy to the power source when the amount of electrical energy stored in the power source is relatively low or the amount of electrical energy stored in the CEC is relatively high. Act 710 can be performed before or after act 705.

In an embodiment, act 710 can include transferring the electrical energy stored from the CEC to the power source via at least one TEC. Transferring the electrical energy stored from the CEC to the power source via at least one TEC can include transferring more or less of the electrical energy from the CEC to the power source than if the TEC is not used.

In an embodiment, act 710 can include, with at least one controller, directing the CEC to transfer at least some of the electrical energy stored therein to the power source. For example, directing the CEC to transfer at least some of the electrical energy stored therein to the power source can include, with the controller, directing the seventh switch (e.g., seventh switch 392 of FIG. 3) to close. For example, directing the CEC to transfer at least some of the electrical energy stored therein to the power source can include, with the controller, directing the CPC of the TEC or another similar device (e.g., DC to DC converter) to allow the electrical energy to flow therethrough.

The method can also include act 715. Act 715 can include biasing the first electrode and the second electrode using at least some of the electrical energy stored in the at least one power source. As such, act 715 can be similar to or the same act 605 of method 600 (FIG. 6). Act 715 can be performed before or after act 705 or act 710.

Figure 8:
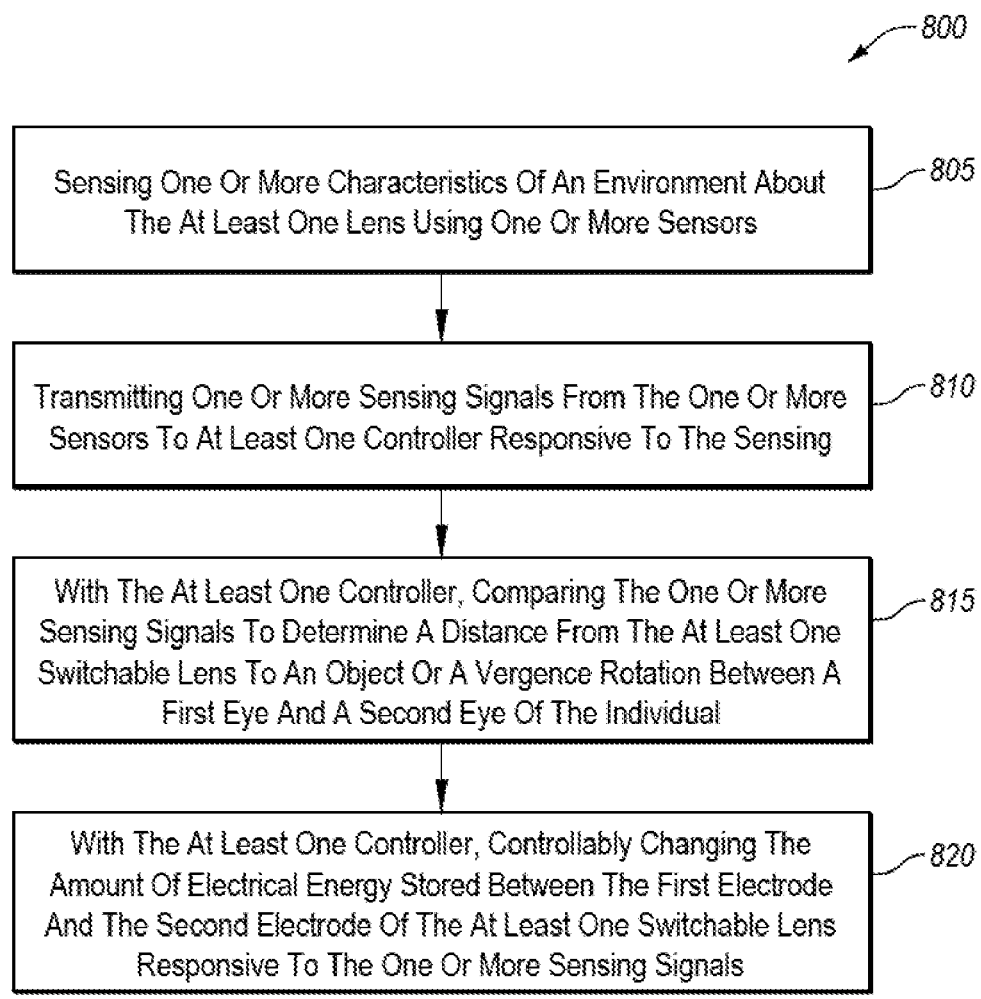

Referring to FIG. 8, the method 800 includes act 805 of sensing one or more characteristics of an environment about the at least one lens using one or more sensors. For example, sensing characteristics of an environment about the switchable lens can include sensing one or more electromagnetic signals with at least one photodetector. For example, sensing characteristics of an environment about the switchable lens can include sensing one or more identifiable magnetic fields with at least one magnetic field sensor. For example, sensing characteristics of an environment about the switchable lens can include sensing one or more electromyography signals with at least two electrodes. For example, sensing characteristics of an environment about the switchable lens can include sensing one or more accelerations of the ophthalmic device with at least one accelerometer.

The method 800 also includes act 810 of transmitting one or more sensing signals from the one or more sensors to at least one controller responsive to the sensing.

The method 800 also includes act 815 that includes, with the at least one controller, comparing the one or more sensing signals to determine a distance from the at least one switchable lens to an object or a vergence rotation between a first eye and a second eye of the individual. For example, comparing sensing signals can include comparing a change in one or more electromagnetic signals (e.g., change in intensity, change in orientation relative to the sensor, etc.) sensed by at least one photodetector. In another example, comparing sensing signals can include comparing a change in one or more identifiable magnetic fields (e.g., change in intensity, change in orientation relative to the sensor, etc.) sensed by at least one magnetic field sensor. In another example, comparing sensing signals can include comparing one or more accelerations of the ophthalmic device (e.g., inward or outward rotation of the first or second eye) sensed by at least one accelerometer. In another example, comparing sensing signals can include comparing one or more electromyography signals sensed by two or more electrodes to determine is the electromyography signals are associated with (e.g., at least partially generated by) a ciliary muscle.

The method 800 also include act 820 that includes, with the at least one controller, controllably changing the amount of electrical energy stored between the first electrode and the second electrode of the at least one switchable lens responsive to the one or more sensing signals. For example, act 820 can include controllably changing the amount of electrical energy stored between the first and second electrodes responsive to the controller determining the apparent object distance or vergence rotation.

In an embodiment, act 820 can include controllably changing the focal length of the switchable lens from a first focal length to a second focal length when the controller determines the apparent object distance or vergence rotation. For example, controllably changing the focal length of the switchable lens from a first focal length to a second focal length can include changing the focal length from a relatively long focal length to a relatively short focal length. For example, controllably changing the focal length of the switchable lens from a first focal length to a second focal length can include changing the focal length from a relatively short focal length to a relatively long focal length.

In an embodiment, act 820 can include transferring electrical energy from the power source to the switchable lens. For example, transferring electrical energy from the power source to the switchable lens can include transferring electrical energy from the power source to the switchable lens using the TEC. In an embodiment, act 820 can include transferring electrical energy from the switchable lens to the CEC. For example, transferring electrical energy from the switchable lens to the CEC can include transferring electrical energy from the switchable lens to the CEC using the TEC. In an embodiment, act 820 can include transferring electrical energy from the CEC to the switchable lens. For example, transferring electrical energy from the CEC to the switchable lens can include transferring electrical energy from the CEC to the switchable lens using the TEC.

Each of the methods 500, 600, 700, 800 can also include transferring at least some of the electrical energy stored in the CEC to one or more components of the ophthalmic device. For example, transferring at least some of the electrical energy stored in the CEC to one or more components of the ophthalmic device can include, with the controller, directing at least the CEC to transfer electrical energy to the one or more components of the ophthalmic device. In another example, transferring at least some of the electrical energy stored in the CEC to one or more components of the ophthalmic device can include transferring the electrical energy stored in the CEC to the controller. For instance, transferring the electrical energy stored in the CEC to the controller can include, with the controller, directing at least the CEC to transfer at least some of the electrical energy stored therein to the controller. In another example, transferring at least some of the electrical energy stored in the CEC to one or more components of the ophthalmic device can include transferring the electrical energy stored in the CEC to the sensors. For instance transferring the electrical energy stored in the CEC to the sensors can include, with the controller, directing at least the CEC to transfer at least some of the electrical energy stored therein to the sensors.

Each of the methods 500, 600, 700, 800 can also include transferring at least some of the electrical energy stored in the power source to one or more components of the ophthalmic device. For example, transferring the electrical energy stored in the power source to the one or more components of the ophthalmic device can include transfer the electrical energy to the CEC, the TEC, the controller, the sensors, etc. For example, transferring the electrical energy stored in the power source to the one or more components of the ophthalmic device can include, with the controller, directing at least the power source to transfer the electrical energy stored therein to the CEC, the TEC, the controller, the sensors, etc.

Each of the methods 500, 600, 700, 800 can also include transmitting one or more signals from the at least one ophthalmic device to the at least one controller or another ophthalmic device. For example, the at least one ophthalmic device can include a first ophthalmic device is a first eye of an individual and a second ophthalmic device in a second eye of the individual, and wherein transmitting the signals from the at least one ophthalmic device to the another ophthalmic device can include transmitting the signals from the first ophthalmic device to the second ophthalmic device. In an embodiment, transmitting the signals from the at least one ophthalmic device can include transmitting status updates, one or more sensing signals, or any other suitable information.

Each of the methods 500, 600, 700, 800 can also include discharging at least some of the electrical energy stored between the first and second electrodes via at least one discharge electrical circuitry. For example, discharging at least some of the electrical energy stored between the first and second electrodes via the discharge electrical circuitry can include discharging substantially all or all of the electrical energy stored between the first and second electrodes via at least one discharge electrical circuitry. For example, discharging at least some of the electrical energy stored between the first and second electrodes via the discharge electrical circuitry can include, with the controller, directing the lens electrical circuitry or the discharge electrical circuitry to discharge at least some of the electrical energy stored between the first and second electrodes via the discharge electrical circuitry.

Each of the methods 500, 600, 700, 800 can also include bypassing electrical energy at least partially around one or more components of the ophthalmic device using at least one bypass electrical circuitry. For example, bypassing electrical energy at least partially around one or more components of the ophthalmic device using the bypass electrical circuitry can include bypassing electrical energy around at least a portion of (e.g., all of) the TEC using the bypass electrical circuitry. For example, bypassing electrical energy around one or more components of the ophthalmic device using the bypass electrical circuitry can include, with the controller, directing at least the bypass electrical circuitry to bypass electrical energy at least partially around the one or more components of the ophthalmic device.

FIGS. 9A-9C are schematic cross-sectional side views of different switchable lenses that can be used in any of the ophthalmic devices disclosed herein, according to various embodiments. Except as otherwise described herein, the switchable lenses 904a-c and their materials, components, or elements can be similar to or the same as the switchable lenses 104, 204, 304, 404 (FIGS. 1-4) and their respective materials, components, or elements. The switchable lenses 904a-c or their materials, components, or elements can be used in any of the ophthalmic devices disclosed herein.

Referring to FIG. 9A, the switchable lens 904a can be a variable focus (e.g., switchable) refractive lens. For example, the switchable lens 904a can include a layer 936a including at least one electro-optical material. The at least one electro-optical material can include any of the electro-optical materials disclosed herein. The layer 936a can include a first outer surface 938a and a second outer surface 940a opposite the first outer surface 938a. The switchable lens 904a can include a first electrode 942a disposed adjacent to (e.g., contact) the first outer surface 938a and a second electrode 944 disposed adjacent to the second outer surface 940a. The first and second electrodes 942a, 944a can apply an electric field to the layer 936a thereby selectively switching the focal length of the switchable lens 904a.

Referring to FIG. 9B, the switchable lens 904b can be a switchable diffractive lens. For example, the switchable lens 904b can include a layer 936b including at least one electro-optical material. The at least one electro-optical material can include any of the electro-optical materials disclosed herein. The layer 936b can include a first outer surface 938b and a second outer surface 940b opposite the first outer surface 938b. The first outer surface 938b can define a diffraction pattern. The switchable lens 904b can include a first electrode 942b disposed adjacent to (e.g., contact) the first outer surface 938b and a second electrode 944b disposed adjacent to the second outer surface 940b. The first electrode 942b can include an inner surface 994 that corresponds to the diffraction pattern. The first and second electrodes 942b, 944*b* can apply an electric field to the layer 936*b* thereby selectively switching the focal length of the switchable lens 904*b*.

Referring to FIG. 9C, the switchable lens 904*c* can be a switchable diffractive lens including two or more layers. For example, the switchable lens 904*c* can include a first layer 936*c* and a second layer 995. At least one of the first or second layers 936*c*, 995 can include at least one electro-optical material. In an embodiment, one of the first or second layers 936*c*, 995 can include a passive material (e.g., a substantially electro-optically inert material). The first layer 936*c* can include a first outer surface 938*c* and a first diffraction surface 996 opposite the first outer surface 938*c*. The first diffraction surface 996 can define a first diffraction pattern. The second layer 995 can include a second outer surface 940*c*. The second outer surface 940*c* is remote from and generally opposing the first outer surface 938*c* of the first layer 936*c*. The second layer 995 can also include a second diffractive surface 998 that is opposite the second outer surface 940*c*. The second diffractive surface 998 can define a second diffraction pattern that is substantially complementary to the first diffraction pattern of the first diffraction surface 996. The switchable lens 904*c* can include a first electrode 942*c* disposed adjacent to (e.g., contact) the first outer surface 938*c* and a second electrode 944*c* disposed adjacent to the second outer surface 940*c*. The first and second electrodes 942*c*, 944*c* can be configured to selectively apply an electric field to the first layer 936*c* or second layer 995 thereby selectively switching the focal length of the switchable lens 904*c*.

Additional examples of switchable lenses are disclosed in U.S. patent application Ser. No. 14/807,673 filed on Jul. 23, 2105, the disclosure of which is incorporated herein, in its entirety, by this reference.

The ophthalmic devices disclosed herein can be any suitable ophthalmic device. FIGS. 10A-10C are schematic illustrations of different ophthalmic devices, according to various embodiments. Except as otherwise described herein, the ophthalmic devices illustrated in FIGS. 10A-10C and their materials, components, or elements can be similar to or the same as the ophthalmic devices 102, 202, 302, or 402 (FIGS. 1-4) and their respective materials, components, or elements. For example, the ophthalmic devices illustrated in FIGS. 10A-10C can include the switchable lens 904*a*, 904*b*, 904*c* (FIGS. 9A-9C). The ophthalmic devices illustrated in FIGS. 10A-10C or their materials, components, or elements can be used in any of the system or ophthalmic device embodiments disclosed herein.

Referring to FIG. 10A, the ophthalmic device 1002*a* can include a spectacle. The spectacle includes two lenses 1004*a*. At least one or both of the two lenses 1004*a* can include any of the switchable lenses disclosed herein. The at least one spectacle include a frame 1005 that at least partially surrounds and supports the two lenses 1004*a*. The spectacle can also include at least one power source 1006*a*, at least one CEC 1008*a*, at least one TEC 1010*a*, and one or more sensors 1016*a*. The spectacle can also include at least one controller 1012*a* coupled to and configured to at least partially control the operation of one or more components of the at least one spectacle. In the illustrated embodiment, the power source 1006*a*, the CEC 1008*a*, the TEC 1010*a*, the controller 1012*a*, and the sensors 1016*a* are at least partially disposed in the frame 1005. However, at least one of the power source 1006*a*, the CEC 1008*a*, the TEC 1010*a*, the controller 1012*a*, or the sensors 1016*a* can be at least partially disposed in at least one of the lenses 1004*a*. For example, the component of the ophthalmic device 1002*a* that is disposed in the lenses 1004*a* can be at least partially transparent (e.g., substantially transparent).

Referring to FIG. 10B, the ophthalmic device 1002*b* can include at least one IOL. The IOL includes a switchable lens 1004*b* and one or more haptics 1007 extending from the switchable lens 1004*b*. The haptics 118 can be configured as wings extending away from the switchable lens 1004*b*. The haptics 1007 can be coupled to the switchable lens 1004*b* to form a multi-piece (e.g., c-loop, j-loop, or modified j-loop) or single piece ophthalmic device 1002*b*. In an embodiment, the haptics 1007 can be configured as arms or struts having an elbow or bend. The arms can be similar to the wings shown in FIG. 10B, with one or more portions of a center of the wings removed therefrom. In an embodiment, the haptics 1007 can be angulated, substantially planar, or offset relative to the switchable lens 1004*b*.

Each of the switchable lens 1004*b* and the haptics 1007 is at least partially formed from any suitable biocompatible material. For example, the switchable lens 1004*b* or the haptics 1007 can include polymethylmethacrylate, hydrophobic acrylic (e.g., a foldable hydrophobic acrylic), a hydrophilic acrylic (e.g., (hydroxyethyl)methacrylate), or a hydrophobic silicone (e.g., polydimethoxysilicone).

The IOL can also include at least one power source 1006*b*, at least one CEC 1008*b*, at least one TEC 1010*b*, and one or more sensors 1016*b*. The IOL can also include at least one controller 1012*b* coupled to and configured to at least partially control the operation of one or more components of the IOL. In the illustrated embodiment, the power source 1006*b*, the CEC 1008*b*, the TEC 1010*b*, the controller 1012*b*, and the sensors 1016*b* are at least partially disposed in at least one of the haptics 1007. However, at least one of the power source 1006*b*, the CEC 1008*b*, the TEC 1010*b*, the controller 1012*b*, or the sensors 1016*b* can be at least partially disposed in the switchable lens 1004*b*. For example, the component of the ophthalmic device 1002*b* that is disposed in the switchable lens 1004*b* can be at least partially transparent (e.g., substantially transparent).

In an embodiment, the ophthalmic device 1002*b* can be used in a system that includes the ophthalmic device 1002*b* and a second IOL. The second IOL can be the same as, similar to, or different from the ophthalmic device 1002*b*. For example, the second IOL can include a switchable lens or a non-switchable lens. The ophthalmic device 1002*b* can be configured to be positioned in a first eye of an individual and the second IOL can be configured to be positioned in a second eye of the individual.

Referring to FIG. 10C, the ophthalmic device 1002*c* can include at least one contact lens configured to be disposed on an eye of an individual. The contact lens includes a switchable lens 1004*c*. The contact lens can also include at least one power source 1006*c*, at least one CEC 1008*c*, at least one TEC 1010*c*, and one or more sensors 1016*c*. The contact lens can also include at least one controller 1012*c* coupled to and configured to at least partially control the operation of one or more components of the contact lens. The power source 1006*c*, the CEC 1008*c*, the TEC 1010*c*, the controller 1012*c*, and the sensors 1016*c* are at least partially disposed in the contact lens. As such, the power source 1006*c*, the CEC 1008*c*, the TEC 1010*c*, the controller 1012*c*, and the sensors 1016*c* can be at least partially transparent (e.g., substantially transparent) or remote from an optical axis, line of sight, visual axis, or the pupillary axis the eye.

In an embodiment, the ophthalmic device 1002*c* can be used in a system that includes the ophthalmic device 1002*c* and another contact lens. The another contact lens can be the same as, similar to, or different from the ophthalmic device 1002*c*. For example, the another contact lens can include a switchable lens or a non-switchable lens. The ophthalmic device 1002*c* can be configured to be positioned on a first eye of an individual and the another contact lens can be configured to be positioned on a second eye of the individual.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein can be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electrical systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context can dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

In an embodiment, the ophthalmic systems disclosed herein can be integrated in such a manner that the ophthalmic systems operate as a unique system configured specifically for function of changing a focal length of a switchable lens, and any associated computing devices of the ophthalmic systems operate as specific use computers for purposes of the claimed system, and not general use computers. In an embodiment, at least one associated computing device of the ophthalmic systems operates as specific use computers for purposes of the claimed system, and not general use computers. In an embodiment, at least one of the associated computing devices of the ophthalmic systems are hardwired with a specific ROM to instruct the at least one computing device. In an embodiment, one of skill in the art recognizes that the ophthalmic devices and ophthalmic systems effects an improvement at least in the technological field of ophthalmic devices.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A system, comprising:
    at least one ophthalmic device including,
        at least one switchable lens including at least one electro-optical material disposed between a first electrode and a second electrode; and
        at least one charging electrical circuitry coupled to the first electrode and the second electrode, the at least one charging electrical circuitry configured to receive and store electrical energy discharged from the first electrode and the second electrode; and
    at least one controller operably coupled to the at least one charging electrical circuitry.

2. The system of claim 1, wherein the at least one ophthalmic device includes at least one spectacle.

3. The system of claim 1, wherein the at least one ophthalmic device includes at least one contact lens or at least one intraocular lens.

4. The system of claim 1, wherein the at least one ophthalmic device includes a first ophthalmic device and a second ophthalmic device, each of the first ophthalmic device and the second ophthalmic device includes a transceiver configured to communicably couple the first ophthalmic device and the second ophthalmic device together.

5. The system of claim 1, wherein the at least one charging electrical circuitry includes a capacitor.

6. The system of claim 1, further comprising at least one transfer electrical circuitry coupled to the at least one charging electrical circuitry, the first electrode, and the second electrode, wherein the at least one transfer electrical circuitry is configured to receive the electrical energy discharged from the first electrode and a second electrode and increase a voltage of the received electrical energy.

7. The system of claim 1, further comprising at least one transfer electrical circuitry coupled to the at least one charging electrical circuitry, the first electrode, and the second electrode, wherein the at least one transfer electrical circuitry is configured to receive the electrical energy stored in the at least one charging electrical circuitry and increase a voltage of the received electrical energy.

8. The system of claim 1, further comprising at least one power source coupled to the first electrode and the second electrode, wherein the at least one power source is distinct from the at least one charging electrical circuitry.

9. The system of claim 8, wherein the at least one power source is coupled to the at least one charging electrical circuitry.

10. The system of claim 9, wherein the at least one controller is configured to direct the at least one charging electrical circuitry to transfer the electrical energy stored in the at least one charging electrical circuitry to the at least one power source.

11. The system of claim 9, further comprising at least one transfer electrical circuitry coupled to the at least one charging electrical circuitry and the power source.

12. The system of claim 8, wherein the at least one power source is operably coupled to the at least one controller, and wherein the at least one controller is configured to direct the at least one power source to bias the first electrode and the second electrode of the at least one ophthalmic device.

13. The system of claim 1, wherein the at least one controller is configured to direct the at least one transfer electrical circuitry to transfer the electrical energy discharged from the first electrode and the second electrode to the at least one charging electrical circuitry.

14. The system of claim 1, wherein the at least one controller is configured to direct the at least one charging electrical circuitry to bias the first electrode and the second electrode.

15. A system, comprising:
    a first ophthalmic device and a second ophthalmic device, each of the first ophthalmic device and second ophthalmic device including,
        at least one switchable lens including at least one electro-optical material disposed between a first electrode and a second electrode; and
        at least one charging electrical circuitry coupled to the first electrode and the second electrode, the at least one charging electrical circuitry configured to receive and store electrical energy discharged from the first electrode and the second electrode; and
    at least one controller operably coupled to the at least one charging electrical circuitry of each of the first ophthalmic device and the second ophthalmic device, the at least one controller configured to,
        direct the at least one charging electrical circuitry to bias the first electrode and the second electrode.

16. The system of claim 15, wherein each of the first ophthalmic device and the second ophthalmic device includes a contact lens or an intraocular lens.

17. The system of claim 15, wherein each of the first ophthalmic device and the second ophthalmic device includes at least one communication device configured to communicably couple the first ophthalmic device and the second ophthalmic device together.

18. The system of claim 15, wherein at least one of the first ophthalmic device or the second ophthalmic device includes at least one transfer electrical circuitry coupled to the at least one charging electrical circuitry, the first electrode, and the second electrode, wherein the at least one controller is operably coupled to the at least one transfer electrical circuitry.

19. The system of claim 18, wherein the at least one transfer electrical circuitry is configured to receive the electrical energy discharged from the first electrode and the second electrode and to increase a voltage of the received electrical energy.

20. The system of claim 18, wherein the at least one transfer electrical circuitry is configured to receive the electrical energy stored in the at least one charging electrical circuitry and to increase a voltage of the received electrical energy.

21. The system of claim 18, wherein the at least one controller is configured to direct the at least one transfer electrical circuitry to transfer the electrical energy discharged from the first electrode and the second electrode to the at least one charging electrical circuitry.

22. The system of claim 15, wherein at least one of the first ophthalmic device or the second ophthalmic device includes at least one power source coupled to the first electrode and the second electrode, wherein the at least one power source is distinct from the at least one charging electrical circuitry.

23. The system of claim 22, wherein the at least one power source is coupled to the at least one charging electrical circuitry.

24. The system of claim 23, wherein the at least one controller is configured to direct the at least one charging electrical circuitry to transfer the electrical energy stored in the at least one charging electrical circuitry to the at least one power source.

25. The system of claim 23, further comprising at least one transfer electrical circuitry coupled to the at least one charging electrical circuitry and the at least one power source.

26. The system of claim 22, wherein the at least one power source is operably coupled to the at least one controller, and wherein the at least one controller is configured to direct the at least one power source to bias the first electrode and the second electrode of the at least one ophthalmic device.

27. The system of claim 15, wherein at least one of the first ophthalmic device or the second ophthalmic device includes one or more sensors configured to sense one or more characteristics.

28. The system of claim 27, wherein the at least one controller is configured to direct at least one of the at least one charging circuitry to receive the electrical energy discharged from the first electrode and the second electrode responsive to the one or more characteristics sensed by the one or more sensors.

29. A method of modifying at least one optical property of at least one switchable lens, the method comprising:
with at least one transfer electrical circuitry, transferring at least some electrical energy stored between a first electrode and a second electrode of the at least one switchable lens to at least one charging electrical circuitry, the at least one charging electrical circuitry configured to receive and store the transferred electrical energy;
wherein the at least one switchable lens includes an electro-optical material disposed between the first electrode and the second electrode.

30. The method of claim 29, further comprising biasing the first electrode and the second electrode with the transferred electrical energy stored in the at least one charging electrical circuitry.

31. The method of claim 29, further comprising biasing the first electrode and the second electrode with electrical energy from at least one power source, wherein the at least one power source is distinct from the at least one charging electrical circuitry.

32. The method of claim 29, further comprising transferring at least some of the transferred electrical energy stored at the at least one charging electrical circuitry to at least one power source, wherein the at least one power source is distinct from the at least one charging electrical circuitry.

* * * * *